(12) United States Patent
Zimmet et al.

(10) Patent No.: US 7,306,920 B2
(45) Date of Patent: Dec. 11, 2007

(54) GENE ASSOCIATED WITH REGULATION OF ENERGY BALANCE, OBESITY AND DIABETES AND USES THEREFOR

(75) Inventors: Paul Zev Zimmet, Toorak (AU); Gregory Collier, Ocean Grove (AU)

(73) Assignees: International Diabetes Institute, Caulfield South, Victoria (AU); Deakin University, Waurn Ponds, Victoria (AU)

( * ) Notice: Subject to any disclaimer, the term of this patent is extended or adjusted under 35 U.S.C. 154(b) by 0 days.

(21) Appl. No.: 10/067,832

(22) Filed: Jun. 3, 2002

(65) Prior Publication Data

US 2005/0059108 A1    Mar. 17, 2005

Related U.S. Application Data

(62) Division of application No. 09/331,930, filed as application No. PCT/AU98/00902 on Oct. 30, 1998, now Pat. No. 6,436,670.

(30) Foreign Application Priority Data

Oct. 31, 1997   (AU) .................................... PP0117
Nov. 11, 1997   (AU) .................................... PP0323

(51) Int. Cl.
  *G01N 33/53*   (2006.01)
  *C07K 14/00*   (2006.01)
(52) U.S. Cl. ........................................ 435/7.1; 530/350
(58) Field of Classification Search .................... None
See application file for complete search history.

(56) References Cited

FOREIGN PATENT DOCUMENTS

WO    WO-00/64931    11/2000

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Wilding, J et al. Increased Neuropeptide-Y Messenger Ribonucleic Acid (mRNA) and Decreased Neurotensin mRNA in the Hypothalamus of the Obese (ob/ob) Mouse. (1993). Endocrinology, vol. 122, No. 5, pp. 1939-1944.*
Barnett, M. et al., "A cross-sectional and short-term longitudinal characterisation of NIDDM in Psammomys obesus," *Diabetologia* (1994) 37:1-6.
Barnett, M. et al., "The effect of restricting energy intake on diabetes in *Psammomys obesus*," *International Journal of Obesity* (1994) 18:1-6.
Barnett, M. et al., "Energy intake with respect to the development of diabetes mellitus in Psammomys obesus," *Diabetes, Nutrition & Metabolium* (1995) 8:42-47.
Bennett, S. A. et al., "Trends in cardiovascular risk factors in Australia," *Medical Journal of Australia* (1994) 161:519-527.

Ciechanover, A. et al., "The ubiquitin-proteasome pathway: The complexity and myriad functions of proteins death," *Proc Natl Acad Sci USA* (1998) 95:2727-2730.
Collier, G. R. et al., "Development of Obesity and Insulin Resistance in the Israeli Sand Rat (*Psammomys obesus*)," *Annals New York Academy of Sciences* (1997a) 827:50-63.
Collier, G. R. et al., "Diabetes, obesity and leptin in the Israeli Sand Rat (*Psammomys obesus*)," *Exp Clin Endocrinol Diabetes* (1997b) 105:36-37.
DeFronzo, R. A., "The Triumvirate: β-Cell, Muscle, Liver," *Diabetes* (1988) 37:667-687.
Kopelman, P. G. et al., "ASO consensus statement on obesity," *Internationl Journal of Obesity* (1994) 18:189-191.
Leibowitz, S. F., "Brain monoamines and peptides: role in the control of eating behavior," *Federation Proc.* (1986) 45:1396-1403.
Liang, P. et al., "Differential display of Eukaryotic Messenger RNA by Means of the Polymerase Chain Reaction," *Science* (1992) 257:967-971.
National Health and Medical Research Council (1996) Acting on Australia's weight: A strategic plan for the prevention of overweight and obesity: Summary Report. Canberra.
Needleman, S. B. et al., "A General Method Applicable to the Search for Similarities in the Amino Acid Sequence of Two Proteins," *J Mol Biol* (1970) 48:443-453.
Ravussin, E., "Metabolic Differences and the Development of Obesity," *Metabolism* (1995) 44:12-14.
Risk Factor Prevalence Study Management Committee. Risk Factor Prevalence Study: Survey No. 3 1989. Canberra: National Heart Foundation of Australia and Australian Institute of Health, 1990.
Shafrir, E. et al., "*Psammomys obesus* of the Jerusalem Colony: a Model for Nutritionally Induced, Non-Insulin-Dependent Diabetes," *Physiology & Pharmacology* (1993) 4:83-99.
Stellar, E., "The physiology of motivation," *Psychological Review* (1954) 61:5-22.
Walder, K. et al., "The Effect of Dietary Energy Restriction on Body Weight Gain and the Development of Noninsulin-Dependent Diabetes Mellitus (NIDDM) in *Psammomys obesus*," *Obesity Research* (1997) 5:193-200.
Walder, K. et al., "Leptin resistance in a polygenic, hyperleptinemic animal model of obesity and NIDDM: *Psammomys obesus*," *International Journal of Obesity* (1999) 23:83-89.
Waters, A-M. et al., "Risk factors for cardiovascular disease: A summary of Australian data," *Cardiovascular Disease Series* Australian Institute of Health & Welfare, 1995.

(Continued)

*Primary Examiner*—Christine J. Saoud
*Assistant Examiner*—Jegatheesan Seharaseyon
(74) *Attorney, Agent, or Firm*—Morrison & Foerster LLP

(57) ABSTRACT

The present invention relates generally to a nucleic acid molecule which encodes a protein associated with the modulation of obesity, diabetes and metabolic energy levels. More particularly, the present invention is directed to a nucleic acid and a recombinant and purified naturally occurring protein encoded thereby and their uses in therapeutic and diagnostic protocols for conditions such as obesity, diabetes and energy imbalance. The subject nucleic acid molecule and protein and their derivatives, homologues, analogues and mimetics are proposed as therapeutic and diagnostic agents for obesity, diabetes and energy imbalance.

3 Claims, 24 Drawing Sheets

OTHER PUBLICATIONS

Zhang, Y. et al., "Position cloning of the mouse obese gene and its human homologue," *Nature* (1994) 372:425-432.

Zimmet, P. Z., "Kelly West Lecture 1991 Challenges in Diabetes Epidermiology—From West to the Rest," *Diabetes Care* (1992) 15:232-252.

Pauley, A. et al. GenBank Nucleotide Sequence Accession No. T25763, Hypothetical Protein F46F11.4 *Caenorhabditis elegans*, 1997.

Marra, M. et al. GenBank Nucleotide Sequence Accession No. AA241830, The WashU_HHMI Mouse EST Project, 1997.

Bray, George, A. (1992) "Peptides Affect the Intake of Specific Nutrients and the Sympathetic Nervous System," *Am. J. Clin. Nutr.* 55; pp. 265-271.

Frankish, Helen M. et al. (1994) "Neuropeptide Y, the Hypothalamus, and Diabetes: Insights Into the Central Control of Metabolism," Peptides 16(4); pp. 757-771.

Marra, M. et al. (1997) "va83b12.r1 Soares Mouse NML Mus Musculus cDNA clone Image: 7379515', mRNA Sequence," retrieved from EBI Database Accession No. AA271476, abstract.

Callis, J. et al. (1995) "Arabidopsis Thaliana Polyubiquitin (ubq8) Gene, Complete Cds," retrieved from EBI Database Accession No. L05917, abstract.

NCI-CGAP, (1997) "ni19g09.s1 NCI_CGAP_Co4 *Homosapiens* cDNA clone Image: 968512 3', mRNA Sequence," retrieved from EBI Database Accession No. AA527091, abstract.

Collier, Greg R. et al. (2000) "A Novel Gene Involved in the Regulation of Energy Balance," *Diabetes* 49, pp. 1766-1771.

Walder, K. et al. (2003) "Obesity and Diabetes Gene Discovery Approaches," *Current Pharmaceutical Design* 9(17), pp. 1357-1372.

Collier, G. et al. (2002) "New Approaches to Gene Discovery with Animal Models of Obesity and Diabetes," *Annals of the New York Academy of Sciences* 967, pp. 403-413.

Walder, K et al. (2001) "Effects of Beacon Administration on Energy Expenditure and Substrate Utilisation in Psammomys obesus (Israeli sand rats), " *International Journal of Obesity* 25, pp. 1281-1285.

\* cited by examiner

3' ATGTTCAACACAGCAGCCATCCAAGTCCTCTAATGTCGAGGTCGGTGT TAC TAA CTC CAC CAA ACG TTG CTG GCA GAT CCT TTC
5' GTTCCAGGAGATTACAGCTCCAGCCACA ATG ATT GAG GTG GTT TGC AAC GAC CGT CTA GGA AAG
                                Met Ile Glu Val Val Cys Asn Asp Arg Leu Gly Lys

TTT CAG GCG CAA TTC ACG TTG TGG CTA CTG TGG CCC CTG TAG CGC CGG GTT TGA CCG TGA GCA
AAA GTC CGC GTT AAG TGC AAC ATC GGG GAC TTG AAG AAA CTG GCG GCC CAA ACT GGC ACT CGT
Lys Val Arg Val Lys Cys Asn Thr Asp Asp Thr Ile Gly Asp Leu Lys Lys Ile Ala Ala Gln Thr Gly Thr Arg

ACC TTA TTC TAG CAA GAA TTT TTC ACC ATG TGC TAA AAA TTC CTG GTA CAT AGA GAC CCT CTA ATA CTT TAG GTG CTA
TGG AAT AAG ATC GTT CTT GAG AAA AAG TGG TAC ACG ATT TTT AAG GAC CAT GTA TCT CTG GGA GAT TAT GAA ATC CAC GAT
Trp Asn Lys Ile Val Leu Lys Lys Trp Tyr Thr Ile Phe Lys Asp His Val Ser Leu Gly Asp Tyr Glu Ile His Asp

CCC TAC CTC GAA ATA ATG GTC ATCTCCCCTTAAGGAGGTGGAACGAAAGGAGAGGTACCGAGTAAATTGT
GGG ATG GAG CTT TAT TAC CAG TAGAGGGAATTCCTCCACCTTGCCAACCTTGCTTTCCTCTCCCATGGCTCATTTAACA
Gly Met Asn Leu Glu Tyr Tyr Gln (SEQ ID NO: 2)

gacaacatctacgagtaaaaattgttaagtgtact 5' (SEQ ID NO: 3)
ctgttgtagatgctcatttttaacaattcacatgataataaaacttgatgctgcaaaaaaaa 3' (SEQ ID NO: 1)

Fig. 1A(i)

```
ATG ATC GAG GTT GTT TGC AAC GAC CGT CTG GGG AAA AAG GTC CNC    45
Met Ile Glu Val Val Cys Asn Asp Arg Leu Gly Lys Lys Val Xaa
 1               5                   10                  15

GTT AAA TGC AAC ACG GAT GAT ACC ATC GGG GAC CTT AAG AAG CTG    90
Val Lys Cys Asn Thr Asp Asp Thr Ile Gly Asp Leu Lys Lys Leu
             20                  25                  30

ATT GCA GCC TAA                                                102
Ile Ala Ala *
```

*Fig.1B*

AMINO ACID ALIGNMENTS

A.

```
                    10         20         30         40         50
                     *          *          *          *          *
Beacon      MIEVVCNDRLGKKVRVKCNTDDTIGDLKKLIAAQTGTRWNKIVLKKWYTI
Human       MIEVVCNDRLGKKVRVKCNTDDTIGDLKKLIAAQTGTRWNKIVLKKWYTI
Mouse       MIEVVCNDRLGKKVRVKCNTDDTIGDLKKLIAAQTGTRWNKIVLKKWYTI
C.elegans   MIEITVNDRLGKKVRIKCNPSDTIGDLKKLIAAQTGTRWEKIVLKKWYTI
F.hepatica           DRLGKKVRVKCNPTDKVGDLKKLIAAQTGTAPERIVLKKWYTI
Rice        MIEVVCNDRLGKKVRVKCNTDDTIGDLKKLIAAQTGTRWNKIVLKKWYTI
S.cerev     MIEVVCNDRLGKKVRVKCNTDDTIGDLKKLIAAQTGTRWNKIVLKKWYTI
```

Fig. 2A (i)

```
                        60              70
                         *               *
Beacon       FKDHVSLGDYEIHDGMNLELYYQ
Human        FKDHVSLGDYEIHDGMNLELYYQ
Mouse        FKDHVSLGDYEIHDGMNLELYYQ
C.elegans    YKDHITLMDYEIHEGFNFELYYQ
F.hepatica   YKDHVTLRDYEINDGMNLELYYQ
Rice         YKDHITLADYEIHDGMGLELYYN
S.cerev      LKDHICLEDYEVHDQTNLELYYL Percentage   homologies
Human        73/73 = 100%
Mouse        73/73 = 100%
C.elegans    59/73 = 81%
F.hepatica   54/66 = 82%
Rice         58/73 = 79%
S.cerev      46/73 = 63%
```

Fig.2A (ii)

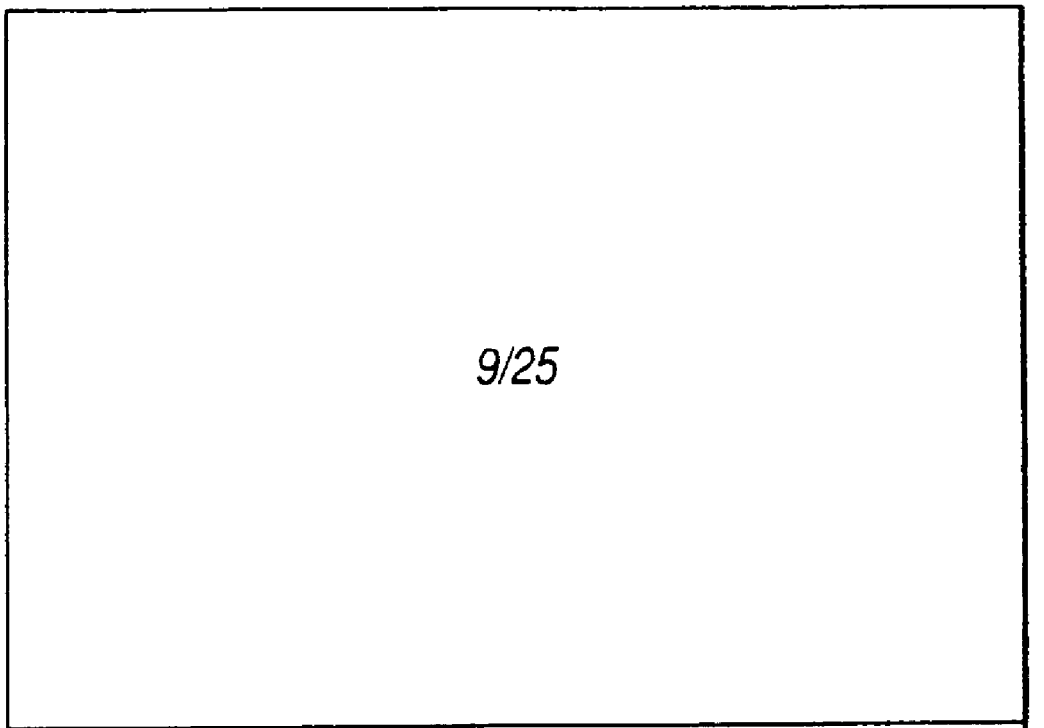
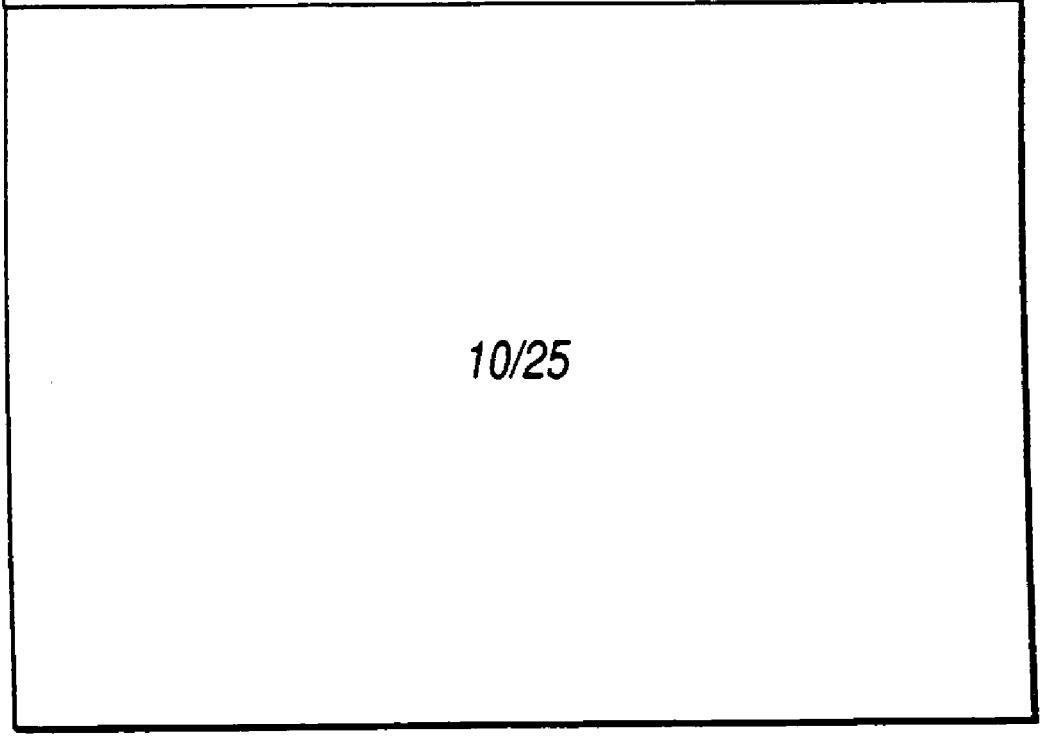
Fig.2B

B.

Human ubiquitin

```
                        10         20         30         40         50
                         *          *          *          *          *
Beacon      MIEVVCNDRLGKKVRVKCNTDDTIGDLKKLIAAQTGTRWNKIVLKKWYTI
               ||  | ++    ||  |||  ++|   +   |  ++|
Ugiquitin   MQIFVKT      LTGKTITLEVEPSDTIENVKAKIQDKEGIPPDQQRLIFAGKQ 60         70
                    *          *
Beacon      FKDHVSLGDYEIHDGMNLELYYQ
             +|  +| ||+|    ||
Ubiquitin   LEDGRTLSDYNIQKESTLHLVLRLRGG
```

Amino acid homology 18/73 = 25%
Positives (similar amino acids) 29/73 = 40%

Fig.2B (i)

Ubiquitin-like protein 8 (A. thaliana)

```
                   10          20          30          40          50
                    *           *           *           *           *
Beacon         MIEVVCNDRLGKKVRVKCNTDDTIGDLKKLIAAQTGTRWNKIVLKKWYTI
               ||  +  +++  +    |||  ++|+   +   |  +    ++ + +  |
A. thaliana                GKTILEVESSDTIANVKEKIQVKEGIKPDQQMLIFFGQQ 60          70
                    *           *
Beacon         FKDHVSLGDYEIHDGMNLELYYQ
               + |  |+|||||+ ||    | |
A. thaliana    LEDGVTLGDYDIHKKSTLYL
```

Amino acid homology 19/60 = 32%
Positives (similar amino acids) 34/60 = 57%

Fig.2B (ii)

★ = significant, p<0.05

* = significant, p<0.05

* = significant, p<0.05

* = significant, p<0.05

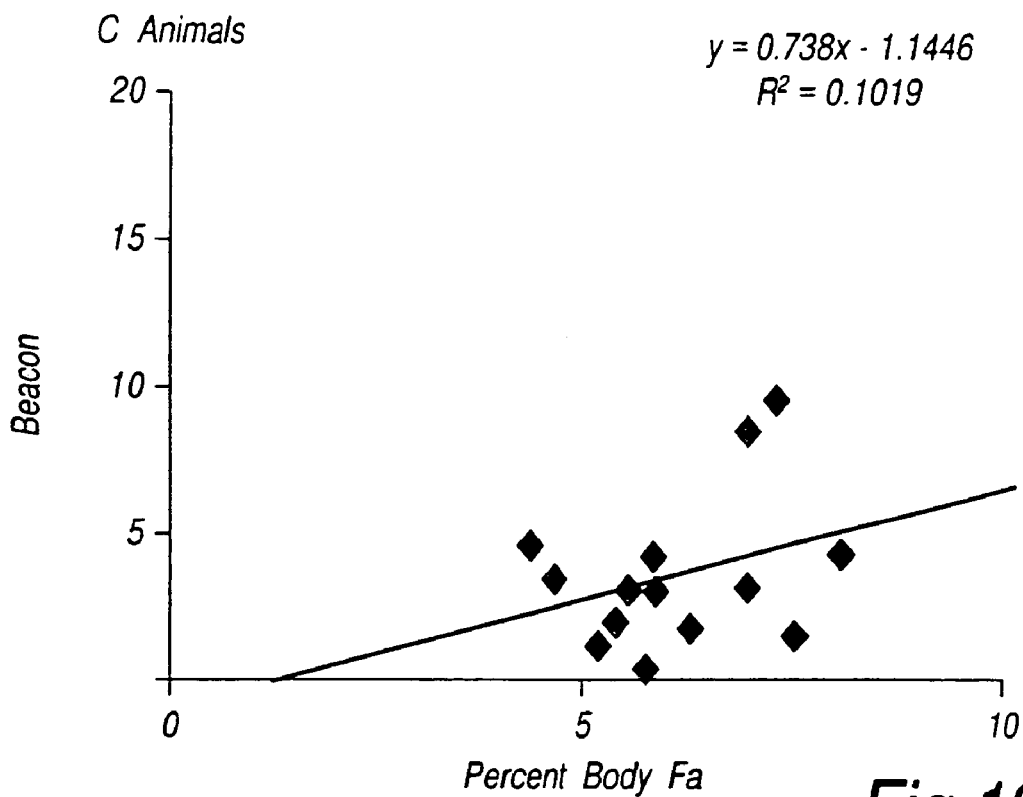
Fig. 13C
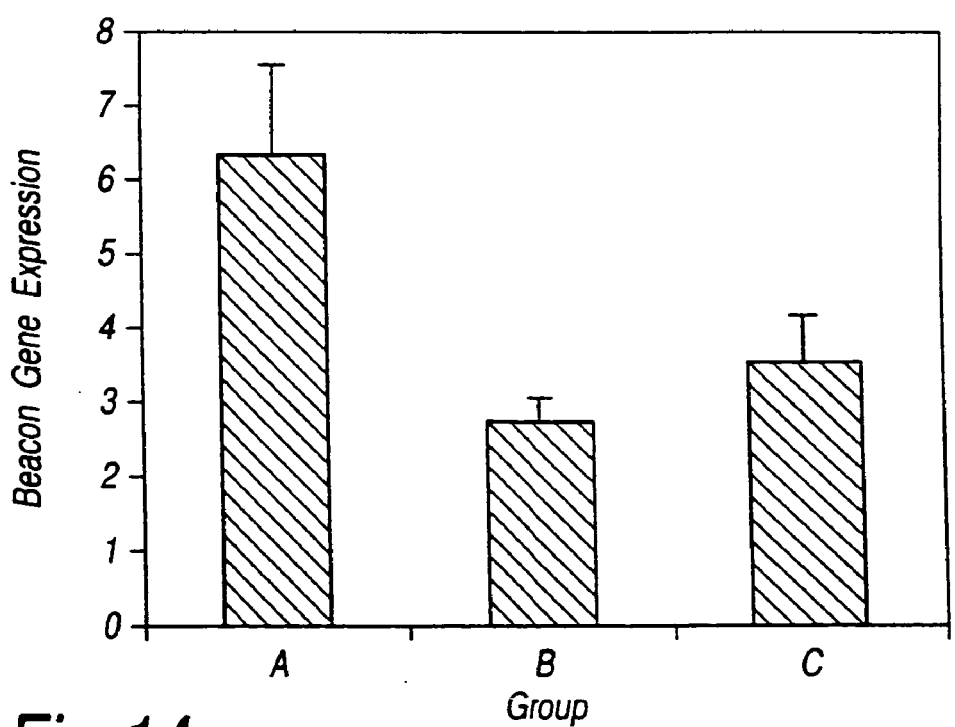
Fig. 14   P<0.01 between Group A and B

GENE ASSOCIATED WITH REGULATION OF ENERGY BALANCE, OBESITY AND DIABETES AND USES THEREFOR

REFERENCE TO RELATED APPLICATIONS

This application is a divisional application of U.S. Ser. No. 09/331,930, filed Jun. 30, 1999, which is a 371 of PCT/AU98/00902, filed Oct. 30, 1998, and resulted in U.S. Pat. No. 6,436,670, the entirety of which is incorporated herein.

FIELD OF THE INVENTION

The present invention relates generally to a nucleic acid molecule which encodes a protein associated with the modulation of obesity, diabetes and metabolic energy levels. More particularly, the present invention is directed to a nucleic acid molecule and a recombinant and purified naturally occurring protein encoded thereby and their use in therapeutic and diagnostic protocols for conditions such as obesity, diabetes and energy imbalance. The subject nucleic acid molecule and protein and their derivatives, homologues, analogues and mimetics are proposed as therapeutic and diagnostic agents for obesity, diabetes and energy imbalance.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Bibliographic details of the publications referred by author in this specification are collected at the end of the description. Sequence Identity Numbers (SEQ ID NOs.) for the nucleotide and amino acid sequences referred to in the specification are defined following the bibliography.

BACKGROUND OF THE INVENTION

The increasing sophistication of recombinant DNA technology is greatly facilitating research and development in the medical, veterinary and allied human and animal health fields. This is particularly the case in the investigation of the genetic bases involved in the etiology of certain disease conditions. One particularly significant condition from the stand point of morbidity and mortality is obesity and its association with non-insulin-dependent diabetes mellitus (NIDDM) and cardiovascular disease.

Obesity is defined as a pathological excess of body fat and is the result of an imbalance between energy intake and energy expenditure for a sustained period of time. Obesity is the most common metabolic disease found in affluent societies. The prevalence of obesity in these nations is alarmingly high, ranging from 10% to upwards of 50% in some subpopulations (Bouchard, 1994). Of particular concern is the fact that the prevalence of obesity appears to be rising consistently in affluent societies and is now increasing rapidly in less prosperous nations as they become more affluent and/or adopt cultural practices from the more affluent countries (Zimmet, 1992).

In Australia, for example, studies using the definition of obesity of BMI>30 have found prevalence rates for obesity of 8.2-9.3% in men and 9.1-11.1% in women (Risk Factor Prevalence Study Management Committee, 1990; Waters and Bennett 1995). The prevalence rates for obesity are increasing in Australia, as they are in many affluent societies. Bennett and Magnus (1994) found that the mean weight of Australian females aged 20-69 increased by 3.1 kg (from 61.7 to 64.8 kg) from 1980 to 1989, while the corresponding increase in males was 1.8 kg (from 77.0 to 78.8 kg). No change in height was observed during this period. Accordingly, the crude prevalence rates of obesity increased from 8.0 to 13.2% in females and from 9.3 to 11.5% in males (Bennett and Magnus 1994). All of the above changes were statistically significant (p<0.05).

The high and increasing prevalence of obesity has significant health implications. Obesity has been identified as a key risk indicator of preventable morbidity and mortality due to disease such as NIDDM and cardiovascular disease (National Health and Medical Research Council, 1996). The annual costs of obesity in Australia, for example, associated with these and other disease conditions have been conservatively estimated at AU$810 million (National Health and Medical Research Council, 1996).

A genetic basis for the etiology of obesity is indicated inter alia from studies in twins, adoption studies and population-based analyses which suggest that genetic effects account for 25-80% of the variation in body weight in the general population (Bouchard 1994; Kopelman et al, 1994; Ravussin, 1995). It is considered that genes determine the possible range of body weight in an individual and then the environment influences the point within this range where the individual is located at any given time (Bouchard, 1994).

Obesity is a complex and heterogeneous disorder and of considerable relevance to society. However, despite numerous studies into genes thought to be involved in the pathogenesis of obesity, there have been surprisingly few significant findings in this area. In addition, genome-wide scans in various population groups have not produced definitive evidence of the chromosomal regions having a major effect on obesity.

The hypothalamus has long been recognised as a key brain area in the regulation of energy intake. Early studies let to the dual-centre hypothesis which propised that two opposing centres in the hypothalamus were responsible for the initiation and termination of eating, the lateral hypothalamus (LHA; "hunger centre") and ventromedial hypothalamus (VMH; "satiety centre"; Stellar 1954). The dual-centre hypothesis has been repeatedly modified to accommodate the increasing information about the roles played by various other brain regions, neurotransmitter systems, and hormonal and neural signals originating in the gut on the regulation of food intake. In addition to the LHA and VMH, the paraventricular nucleus (PVN) is now considered to have an important integrative function in the control of energy intake.

A large number of neurotransmitters have been investigated as possible hypothalamic regulators of feeding behaviour including neuropeptide Y (NPY), glucagon-like peptide 1 (GLP-1), melanin-concentrating hormone (MCH), serotonin, cholecystokinin and galanin. Some of these neurotransmitters stimulate food intake, some act in an anorexigenic manner and some have diverse effects on energy intake depending on the site of administration. For example, gamma-aminobutyric acid (GABA) inhibits food intake when injected into the LHA, but stimulates eating when injected into the VMH or PVN (Leibowitz, 1985). Feeding behaviour is thought to be greatly influenced by the interaction of stimulatory and inhibitory signals in the hypothalamus.

In work leading up to the present invention, the inventors have made a significant break through in determining a genetic basis of obesity by identifying a genetic sequence differentially expressed in lean and obese animals. In accordance with the present invention, the inventors have isolated a novel gene which is proposed to be associated with energy balance and also in modulating obesity and diabetes.

SUMMARY OF THE INVENTION

One aspect of the present invention provides a nucleic acid molecule comprising a sequence of nucleotides encoding or complementary to a sequence encoding a protein or a derivative, homologue, analogue or mimetic thereof wherein said nucleic acid molecule is expressed in larger amounts in hypothalamus tissue of obese animals compared to lean animals.

Another aspect of the present invention is directed to a nucleic acid molecule comprising a nucleotide sequence, or a complementary form thereof, encoding an amino acid sequence substantially as set forth in SEQ ID NO:2 or SEQ ID NO:14 or an amino acid sequence having at least 30% similarity to all or a part thereof or a mimetic or said amino acid sequence or a nucleotide sequence capable of hybridizing to said nucleic acid molecule under low stringency conditions at 42° C. and wherein said nucleic acid molecule is expressed in a larger amount in hyperthalamus tissue of obese animals compared to lean animals.

Yet another aspect of the present invention provides a nucleic acid molecule comprising a nucleotide sequence encoding or complementary to a sequence encoding a protein or a derivative, homologue, analogue or mimetic thereof wherein said nucleotide sequence is as substantially set forth in SEQ ID NO:1 or SEQ ID NO:13 or a nucleotide sequence having at least about 30% similarity to all or part of SEQ ID NO:1 or SEQ ID NO:13 and/or is capable of hybridizing to SEQ ID NO:1 or SEQ ID NO:13 under low stringency conditions at 42° C. and wherein said nucleic acid molecule is expressed in a larger amount in hyperthalamus tissue of obese animals compared to lean animals.

Still yet another aspect of the present invention provides an isolated protein or a derivative, homologue, analogue or mimetic thereof which is produced in a larger amount in hyperthalamus tissue of obese animals compared to lean animals.

In yet another aspect of the present invention, there is provided an isolated protein or a derivative, homologue, analogue or mimetic thereof wherein said protein comprises an amino acid sequence substantially as set forth in SEQ ID NO:2 or SEQ ID NO:14 or an amino acid sequence having at least 30% similarity to all or part of SEQ ID NO:2 or SEQ ID NO:14 and wherein said protein is produced in a larger amount in hyperthalamus tissue of obese animals compared to lean animals.

A further aspect of the present invention is directed to an isolated protein or a derivative, homologue, analogue or mimetic thereof wherein said protein is encoded by a nucleotide sequence substantially as set forth in SEQ ID NO:1 or SEQ ID NO:13 or a nucleotide sequence having at least 60% similarity to all or part of SEQ ID NO:1 or SEQ ID NO:13 and/or is capable of hybridizing to SEQ ID NO:1 or SEQ ID NO:13 under low stringency conditions at 42° C.

The protein of the present invention is referred to as "beacon" and the nucleotide sequence encoding beacon is referred to as the beacon gene.

A further aspect of the present invention relates to a composition comprising beacon or its derivatives, homologues, analogues or mimetics or agonists or antagonists of beacon together with one or more pharmaceutically acceptable carriers and/or diluents.

Yet a further aspect of the present invention contemplates a method for treating a subject comprising administering to said subject a treatment effective amount of beacon or a derivative, homologue, analogue or mimetic thereof or a genetic sequence encoding same or an agonist or antagonist of beacon or beacon gene expression for a time and under conditions sufficient to effect treatment.

In accordance with this and other aspects of the present invention, treatments contemplated herein include but are not limited to obesity, anorexia, weight maintenance, energy imbalance and diabetes. Treatment may be by the administration of a pharmaceutical composition or genetic sequences via gene therapy. Treatment is contemplated for human subjects as well as animals such as animals important to livestock industry.

Still yet another aspect of the present invention is directed to a diagnostic agent for use in monitoring or diagnosing conditions such as but not limited to obesity, anorexia, weight maintenance, energy imbalance and/or diabetes, said diagnostic agent selected from an antibody to beacon or its derivatives, homologues, analogues or mimetics and a genetic sequence useful in PCR, hybridization, RFLP amongst other techniques.

A summary of SEQ ID NOs used throughout the subject specification is provided in Table 1.

TABLE 1

| SEQ ID NO. | DESCRIPTION |
|---|---|
| 1 | Nucleotide sequence for beacon |
| 2 | Amino acid sequence for beacon |
| 3 | Complementary sequence for SEQ ID NO: 1 |
| 4 | Primer sequence |
| 5 | Primer sequence |
| 6 | Primer sequence |
| 7 | Primer sequence |
| 8 | Primer sequence |
| 9 | Primer sequence |
| 10-12 | Primer and probe sequences used for beacon gene expression studies |
| 13 | Nucleotide sequence for human beacon |
| 14 | Amino acid sequence for human beacon ("short" form of beacon) |

A summary of the single and three letter abbreviations for amino acid residues used in the present specification is provided in Table 2.

TABLE 2

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |

TABLE 2-continued

| Amino Acid | Three-letter Abbreviation | One-letter Symbol |
|---|---|---|
| Valine | Val | V |
| Any residue | Xaa | X |

BRIEF DESCRIPTION OF THE DRAWINGS

FIG. 1A(i) is a representation showing the nucleotide sequence of both strands (SEQ ID NO: 1 which encodes the protein and SEQ ID NO: 3, respectively in order of appearance) of a differentially expressed band in hypothalamus tissue of lean and obese Psammomys obesus corresponding to beacon. The amino acids encoded by each codon are shown above in single letter code (SEQ ID NO: 2) and the numbering refers to the amino acid position from the start codon.

FIG. 1B is a representation of a nucleotide (SEQ ID NO: 13) and corresponding amino acid sequence (SEQ ID NO: 14) of human beacon. Human beacon is a "short" form of Psammomys obesus beacon except that amino acid 15 may be His or Arg. The corresponding codon may be CGC or CAC, respectively.

FIG. 14 is a graphical representation showing beacon gene expression in Group A, B and C Psammomys obesus.

DETAILED DESCRIPTION OF THE PREFERRED EMBODIMENTS

Figure 2A:
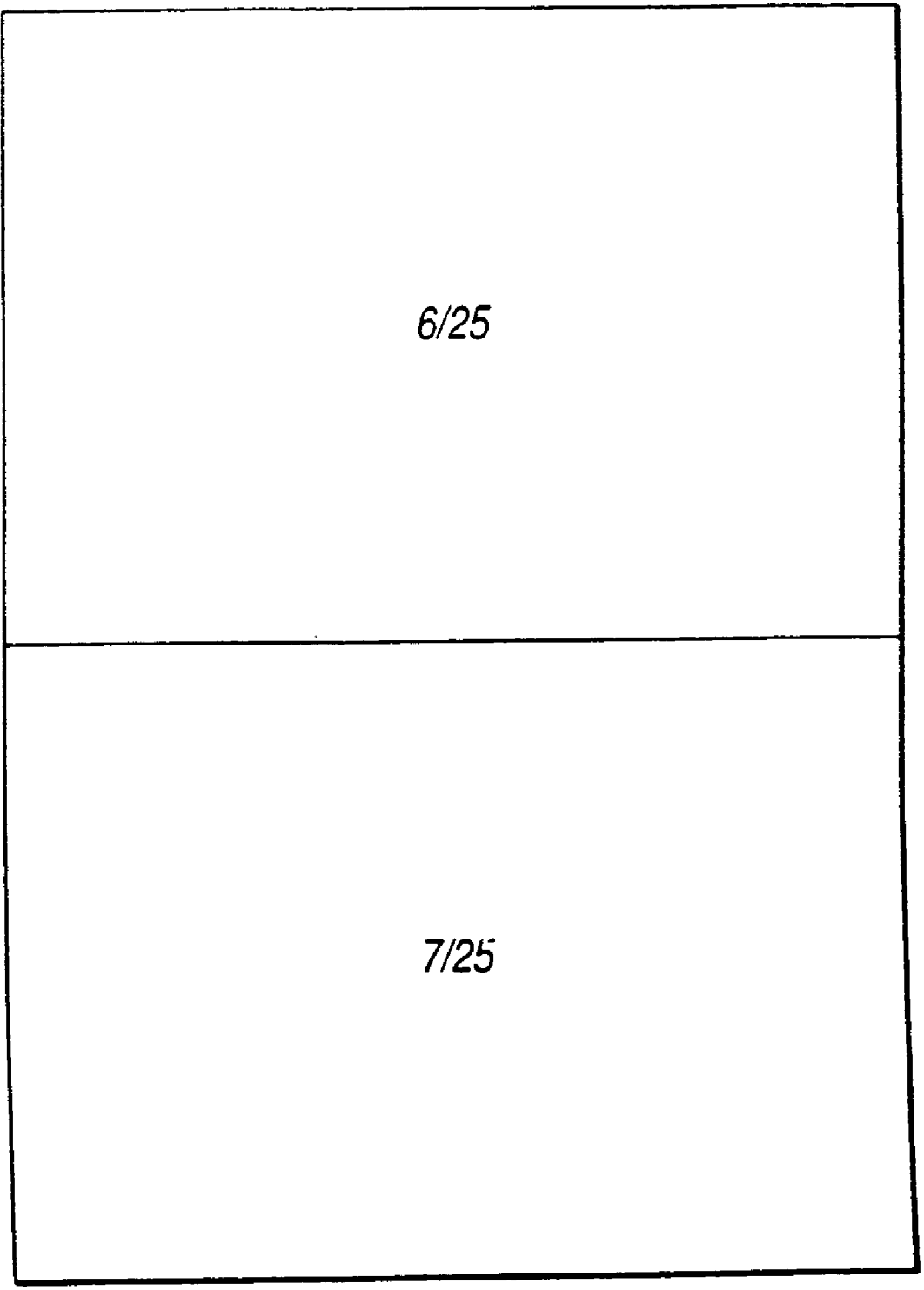
FIG. 2 is a representation showing (A). Amino acid alignments of beacon (SEQ ID NO: 2) with putative human (SEQ ID NO: 15), mouse (SEQ ID NO: 16), Caenorhabditis elegans (SEQ ID NO: 17), Fasiola hepatica (SEQ ID NO: 18), rice (SEQ ID NO: 19) and Saccharomyes cerevisiae (SEQ ID NO: 20) gene products. (B). Amino acid alignments of beacon (SEQ ID NO: 2 shown as the top sequence twice) with human ubiquitin (SEQ ID NO: 21) and ubiquitin-like protein 8 from Arabidopsis thaliana (SEQ ID NO: 22). Identical amino acids are marked with a line and plus signs indicate deletions are indicated by forward slashes. A spliced leader sequence in the F. hepatica gene did not allow the amino terminal amino acids to be compared.

The present invention is predicated in part on the identification of a novel gene associated inter alia with regulation of energy balance obesity and diabetes. The gene was identified following differential screening of hypothalamic mRNA between lean and obese animals.

Accordingly, one aspect of the present invention provides a nucleic acid molecule comprising a sequence of nucleotide encoding or complementary to a sequence encoding a protein or a derivative homologue, analogue or mimetic thereof wherein said nucleic acid molecule is expressed in a larger amount in hypothalamus tissue of obese animals compared to lean animals.

The terms "lean" and "obese" are used in their most general sense but should be considered relative to the standard criteria for determining obesity. Generally, for human subjects the definition of obesity is BMI>30 (Risk Factor Prevalence 1990; Waters and Bennett, 1995).

Conveniently, an animal model may be employed to study the effects of obese and lean animals. In particular, the present invention is exemplified using the Psammomys obesus (the Israeli sand rat) animal model of dietary-induced obesity and NIDDM. In its natural desert habitat, an active lifestyle and saltbush diet ensure that they remain lean and normoglycernic (Shafrir and Gutman, 1993). However, in a laboratory setting on a diet of ad libitum chow (on which many other animal species remain healthy), a range of pathophysiological responses are seen (Barnett et al, 1994a, b; Barnett et al, 1995). By the age of 16 weeks, more than half of the animals become obese and approximately one third develop NIDDM. Only hyperphagic animals go on to develop hyperglycemia, highlighting the importance of excessive energy intake in the pathophysiology of obesity and NIDDM in Psammomys obesus (Collier et al, 1997a; Walder et al, 1997a). Other phenotypes found include hyperinsulinemia, dyslipidemia and impaired glucose tolerance (Collier et al, 1997a, b). Psammomys obesus exhibit a range of bodyweight and blood glucose and insulin levels which forms a continuous curve that closely resembles the patterns found in human populations, including the inverted U-shaped relationship between blood glucose and insulin levels known as "Starling's curve of the pancreas" (Barnett et al, 1994a; DeFronzo, 1988). It is the heterogeneity of the phenotypic response of *Psammomys obesus* which make it an ideal model to study the etiology and pathophysiology of obesity and NIDDM.

A preferred embodiment of the present invention is directed to a nucleic acid molecule comprising a nucleotide sequence or a complementary form thereof encoding an amino acid sequence substantially as set forth in SEQ ID NO:2 or SEQ ID NO:14 or an amino acid sequence having at least 60% similarity to all or a part thereof or is a mimetic thereof or a nucleotide sequence capable of hybridizing to said nucleic acid molecule under low stringency conditions at 42° C. and wherein said nucleic acid molecule is expressed in larger amounts in hyperthalamus tissue of obese animals compared to lean animals.

Another embodiment of the present invention provides a nucleic acid molecule comprising a nucleotide sequence encoding or complementary to a sequence encoding a protein or a derivative, homologue, analogue or mimetic thereof wherein said nucleotide sequence is as substantially set forth in SEQ ID NO:1 or SEQ ID NO:13 or a nucleotide sequence having at least about 60% similarity to all or part of SEQ ID NO:1 or SEQ ID NO:13 and/or is capable of hybridizing to SEQ ID NO:1 or SEQ ID NO:13 under low stringency conditions at 42° C. and wherein said nucleic acid molecule is expressed in a larger amount in hyperthalamus tissue of obese animals compared to lean animals.

Reference herein to similarity is generally at a level of comparison of at least 15 consecutive or substantially consecutive nucleotides or at least 5 consecutive or substantially consecutive amino acid residues.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch (1970). Gap reads a scoring matrix that contains values for every possible GCG symbol match. GAP is available on ANGIS (Australian National Genomic Information Service) at website http://mell.angis.org.au.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

The nucleotide sequence or amino acid sequence of the present invention may correspond to exactly the same sequence of the naturally occurring gene (or corresponding cDNA) or protein or may carry one or more nucleotide or amino acid substitutions, additions and/or deletions. The nucleotide sequence set forth in SEQ ID NO:1 or SEQ ID NO:13 corresponds to a new gene referred to herein as "beacon". The corresponding protein is "beacon". Reference herein to beacon includes, where appropriate, reference to the genomic gene or cDNA as well as any naturally occurring or induced derivatives. Apart from the substitutions, deletions and/or additions to the nucleotide sequence, the present invention further encompasses mutants, fragments, parts and portions of the nucleotide sequence corresponding to beacon. One useful form of a beacon encodes a "short" form of beacon. The short form of beacon corresponds to human beacon. The preferred short form of beacon is 33 amino acids in length. Such a short form can also be readily synthesised in vitro.

A homologue is considered to be a beacon gene from another animal species. The beacon gene is exemplified herein from *Psammomys obesus* hypothalamus. The invention extends, however, to the homologous gene, as determined by nucleotide sequence and/or function, from humans, primates, livestock animals (eg. cows, sheep, pigs, horses, donkeys), laboratory test animals (eg. mice, guinea pigs, hamsters, rabbits), companion animals (eg. cats, dogs) and captured wild animals (eg. rodents, foxes, deer, kangaroos).

The nucleic acid of the present invention and in particular beacon and its derivatives and homologues may be in isolated or purified form and/or may be ligated to a vector such as an expression vector. Expression may be in a eukaryotic cell line (eg. mammalian, insect or yeast cells) or in microbial cells (eg. *E. coli*) or both.

The derivatives of the nucleic acid molecule of the present invention include oligonucleotides, PCR primers, antisense molecules, molecules suitable for use in co-suppression and fusion nucleic acid molecules. Ribozymes and DNA enzymes are also contemplated by the present invention directed to beacon or its mRNA. Derivatives and homologues of beacon are conveniently encompassed by those nucleotide sequences capable of hybridizing to SEQ ID NO:1 or SEQ ID NO:13 or 3 under low stringency conditions at 42° C.

Another aspect of the present invention provides an isolated protein or a derivative, homologue, analogue or mimetic thereof which is produced in larger amounts in hyperthalamus tissue in obese animals compared to lean animals.

In a more preferred aspect of the present invention, there is provided an isolated protein or a derivative, homologue, analogue or mimetic thereof wherein said protein comprises an amino acid sequence substantially as set forth in SEQ ID NO:2 or SEQ ID NO:14 or an amino acid sequence having at least 60% similarity to all or part of SEQ ID NO:2 or SEQ ID NO:14 and wherein said protein is produced in larger amounts by hyperthalamus tissue of obese animals compared to lean animals.

A further aspect of the present invention is directed to an isolated protein or a derivative, homologue, analogue or mimetic thereof wherein said protein is encoded by a nucleotide sequence substantially as set forth in SEQ ID NO:1 or SEQ ID NO:13 or a nucleotide sequence having at least 60% similarity to all or part of SEQ ID NO:1 or SEQ ID NO:13 and/or is capable of hybridizing to SEQ ID NO:1 or SEQ ID NO:13 under low stringency conditions at 42° C. The protein of this aspect of the present invention is beacon. A truncated form of beacon is referred to as a "short form". The preferred short form is 33 amino acids in length. Reference herein to beacon includes reference to isolated or purified naturally occurring beacon protein molecules as well as any derivatives, homologues, analogues and mimetics thereof. Derivatives includes parts, fragments and portions of beacon as well as single and multiple amino acid substitutions, deletions and/or additions to beacon. A derivative of beacon is conveniently encompassed by molecules encoded by a nucleotide sequence capable of hybridizing to SEQ ID NO:1 or SEQ ID NO:13 under low stringency conditions at 42° C.

Other derivatives of beacon include chemical analogues. Analogues of beacon contemplated herein include, but are not limited to, modifications to side chains, incorporation of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

TABLE 3

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |

TABLE 3-continued

| Non-conventional amino acid | Code | Non-conventional amino acid | Code |
|---|---|---|---|
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenylethylamino) cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

All such modifications may also be useful in stabilizing the beacon molecule for use in in vivo administration protocols or for diagnostic purposes.

The identification of beacon permits the generation of a range of therapeutic molecules capable of modulating expression of beacon or modulating the activity of beacon. Modulators contemplated by the present invention includes agonists and antagonists of beacon expression. Antagonists of beacon expression include antisense molecules, ribozymes and co-suppression molecules. Agonists include molecules which increase promoter activity or which interfere with negative regulatory mechanisms. Antagonists of beacon include antibodies and inhibitor peptide fragments. All such molecules may first need to be modified to enable such molecules to penetrate cell membranes. Alternatively, viral agents may be employed to introduce genetic elements to modulate expression of beacon. In so far as beacon acts in association with other genes such as the ob gene which encodes leptin, the therapeutic molecules may target both the beacon and ob genes or their translation products.

The present invention contemplates, therefore, a method for modulating expression of beacon in a mammal, said method comprising contacting the beacon gene with an effective amount of a modulator of beacon expression for a time and under conditions sufficient to up-regulate or down-regulate or otherwise modulate expression of beacon. For example, a nucleic acid molecule encoding beacon or a derivative or homologue thereof may be introduced into a cell to enhance the ability of that cell to produce beacon, conversely, beacon antisense sequences such as oligonucleotides may be introduced to decrease the availability of beacon molecules.

Another aspect of the present invention contemplates a method of modulating activity of beacon in a mammal, said method comprising administering to said mammal a modulating effective amount of a molecule for a time and under conditions sufficient to increase or decrease beacon activity. The molecule may be a proteinaceous molecule or a chemical entity and may also be a derivative of beacon or its ligand.

Modulating levels of beacon expression is important in the treatment of a range of conditions such as obesity, anorexia, energy imbalance, diabetes, metabolic syndrome, dyslipidemia, hypertension and insulin resistance. It may also be useful in the agricultural industry to assist in the generation of leaner animals, or where required, more obese animals. Accordingly, the mammal contemplated by the present invention includes but is not limited to humans, primates, livestock animals (eg. pigs, sheep, cows, horses, donkeys), laboratory test animals (eg. mice, rats, guinea pigs, hamsters, rabbits), companion animals (eg. dogs, cats) and captured wild animals (eg. foxes, kangaroos, deer). A particularly preferred host is a human, primate or livestock animal.

Accordingly, the present invention contemplates in one embodiment a composition comprising a modulator of beacon expression or beacon activity and one or more pharmaceutically acceptable carriers and/or diluents. In another embodiment, the composition comprises beacon or a derivative, homologue, analogue or mimetic thereof and one or more pharmaceutically acceptable carriers and/or diluents. The compositions may also comprise leptin or modulations of leptin activity or ob expression.

For brevity, all such components of such a composition are referred to as "active components".

The compositions of active components in a form suitable for injectable use include sterile aqueous solutions (where water soluble) and sterile powders for the extemporaneous preparation of sterile injectable solutions. In all cases, the form must be sterile and must be fluid to the extent that easy syringability exists. It must be stable under the conditions of manufacture and storage and must be preserved against the contaminating action of microorganisms such as bacteria and fungi.

The carrier can be a solvent or other medium containing, for example, water, ethanol, polyol (for example, glycerol, propylene glycol and liquid polyethylene glycol, and the like), suitable mixtures thereof, and vegetable oils.

The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active components in the required amount in the appropriate solvent with optionally other ingredients, as required, followed by sterilization by, for example, filter sterilization, irradiation or other convenient means. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When beacon and beacon including beacon itself are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active component may be compounded for convenient and effective administration in sufficient amounts with a suitable pharmaceutically acceptable carrier in dosage unit form. A unit dosage form can, for example, contain the principal active component in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

In general terms, effective amounts of beacon will range from 0.01 ng/kg/body weight to above 10,000 mg/kg/body weight. Alternative amounts range from 0.1 ng/kg/body weight is above 1000 mg/kg/body weight. Beacon may be administered per minute, hour, day, week, month or year depending on the condition being treated. The route of administration may vary and includes intravenous, intraperitoneal, subcutaneous, intramuscular, intranasal, via suppository, via infusion, via drip, orally or via other convenient means.

The pharmaceutical composition may also comprise genetic molecules such as a vector capable of transfecting target cells where the vector carries a nucleic acid molecule capable of modulating beacon expression or beacon activity. The vector may, for example, be a viral vector.

Still another aspect of the present invention is directed to antibodies to beacon and its derivatives and homologues. Such antibodies may be monoclonal or polyclonal and may be selected from naturally occurring antibodies to beacon or may be specifically raised to beacon or derivatives or homologues thereof. In the case of the latter, beacon or its derivatives or homologues may first need to be associated with a carrier molecule. The antibodies and/or recombinant beacon or its derivatives of the present invention are particularly useful as therapeutic or diagnostic agents.

For example, beacon and its derivatives can be used to screen for naturally occurring antibodies to beacon which may occur in certain autoimmune diseases or where cell death is occurring. These may occur, for example in some autoimmune diseases. Alternatively, specific antibodies can be used to screen for beacon. Techniques for such assays are well known in the art and include, for example, sandwich assays and ELISA.

Antibodies to beacon of the present invention may be monoclonal or polyclonal and may be selected from naturally occurring antibodies to the beacon or may be specifically raised to the beacon or its derivatives. In the case of the latter, the beacon protein may need first to be associated with a carrier molecule. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool or as a means for purifying beacon.

For example, specific antibodies can be used to screen for beacon proteins. The latter would be important, for example, as a means for screening for levels of beacon in a cell extract or other biological fluid or purifying beacon made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of beacon.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of beacon, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, Nature 256: 495-499, 1975; *European Journal of Immunology* 6: 511-519, 1976).

Another aspect of the present invention contemplates a method for detecting beacon or a derivative or homologue thereof in a biological sample from a subject said method comprising contacting said biological sample with an antibody specific for beacon or its antigenic derivatives or homologues for a time and under conditions sufficient for a complex to form, and then detecting said complex.

The presence of the complex is indicative of the presence of beacon. This assay may be quantitated or semi-quantitated to determine a propensity to develop obesity or other conditions or to monitor a therapeutic regimum.

The presence of beacon may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays. A number of variations of the sandwich assay technique exist, and all are intended to be encompassed by the present invention. Briefly, in a typical forward assay, an unlabeled antibody is immobilized on a solid substrate and the sample to be tested brought into contact with the bound molecule. After a suitable period of incubation, for a period of time sufficient to allow formation of an antibody-beacon complex, a second antibody specific to the beacon, labelled with a reporter molecule capable of producing a detectable signal, is then added and incubated, allowing time sufficient for the formation of another complex of antibody-beacon-labelled antibody. Any unreacted material is washed away, and the presence of the beacon is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain beacon including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to about 37° C.) to allow binding of any subunit present in the antibody. Following the incubation period, the antibody subunit solid phase is washed and dried and incubated with a second antibody specific for a portion of beacon. The second antibody is linked to a reporter molecule which is used to indicate the binding of the second antibody to beacon.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemilumninescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactodidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. A "reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect beacon or its derivatives.

The assays of the present invention may also extend to measuring beacon or beacon in association with ob or leptin.

The present invention is further described by reference to the following non-limiting Examples.

EXAMPLE 1

Animals

A *Psammomys obesus* colony is maintained at Deakin University, with the breeding pairs fed ad libitum a diet of lucerne and chow. Experimental animals were weaned at four weeks of age and given a diet of standard laboratory chow from which 12% of energy was derived from fat, 63% from carbohydrate and 25% from protein (Barastoc, Pakenham, Australia). Animals were housed individually in a temperature controlled room (22±1° C.) with a 12-12-hour light-dark cycle. The animals used in the study were aged 16-20 weeks during the pretreatment period. A total of 30 *Psammomys obesus* were investigated in this study, of which 10 were treated with leptin as described below and 20 were used as controls (treated with saline only).

EXAMPLE 2

Leptin Treatment

A group of lean and obese *Psammomys obesus* were followed for a 7-day period with free access to food and water to establish baseline data for food intake (measured by the rate of disappearance), body weight, blood glucose and plasma insulin concentrations. After the baseline period, the animals were given intraperitoneal injections three times per day (at 0800, 1600 and 2400) of 15 mg leptin per kg body weight, or equivalent volume of saline for control animals, for a total of 7 days. This dosage of leptin resulted in a total of 45 mg/kg/day. Body weight and food intake were measured daily throughout the study. In addition, blood was collected from the animals on days 2, 4 and 7 at midday (the midpoint between the morning and afternoon injections) for biochemical analyses. The results clearly demonstrated that leptin was effective in reducing body weight and food intake in the lean animals, however, the obese animal remained leptin resistant and demonstrated no differences in food intake or body weight (Walder et al 1997b).

EXAMPLE 3

Nicotine Treatment

As described above for the leptin treatment, animals were followed for a 1 week run in period before being allocated to either infusion with 12 mg/day nicotine or vehicle control infusion for 7 days. All infusions were via mini-osmotic pumps implanted subcutaneously (Alza, Calif., USA). Nicotine treatment resulted in a significant reduction in food intake and body weight, this effect was more pronounced than the effect of leptin described above and occurred in both lean and obese animals.

At the completion of either study the animals were killed by anaesthetic overdose (120 mg/kg pentobarbitone) and selected fat depots (interscapular, perirenal, epididymal, mesenteric and intramuscular) were removed and weighed to allow an estimate of body fat content. The weights of the various fat depots were combined and divided by total body mass to provide this estimate.

All of the experiments described above were carried out following the Australian NHMRC principles of laboratory animal care and approved by the Deakin University Animal Ethics Committee, Deakin University, Geelong.

EXAMPLE 4

Analytical Methods

Whole blood glucose was measured using an enzymatic glucose analyser (Model 27, Yellow Springs Instruments, Ohio). Plasma insulin concentrations were determined using a double antibody solid phase radioimmunoassay (Phadeseph, Kabi Pharmacia Diagnostics, Sweden).

EXAMPLE 5

Differential Display Polymerase Chain Reaction (ddPCR)

mRNA was extracted from the hypothalamus using a Dynabeads mRNA DIRECT kit (Dynal, Oslo, Norway). The mRNA was reverse transcribed to form cDNA using the oligo-dT primer attached to the beads and AMV reverse transcriptase (Promega, Madison, Wis.). The ddPCR procedure developed by Liang and Pardee (1992) was modified such that second strand cDNA was produced using arbitrary 13 mers and then used for the PCR reaction with the same arbitrary primer and three one-base-anchored oligo-dT primers. All primers were obtained from GenHunter Corporation (Nashville, Tenn.). The sequence of the primers that gave the beacon gene PCR product were 5'-AAGCTTTTTTTTTTTG-3' [SEQ ID NO:4] (G-anchored primer) and 5'-AAGCTTCGGGTAA-3' [SEQ ID NO:5] (arbitrary primer 11). The 20 µl second strand cDNA synthesis reaction contained 200 nM arbitrary primer, 12.5 µM dNTPs, 100 mM Tris-HCl (pH 8.4), 50 mM KCl, 1.5 mM $MgCl_2$, 0.001% gelatin and 1 unit Taq DNA polymerase (Qiagen, Hilden, Germany). Denaturation was performed at 94° C. for one minute, annealling at 40° C. for 2 minutes and elongation at 72° C. for 5 minutes. The reactions were then placed at 94° C. for 2 minutes to separate the 2 strands of cDNA and the second strand removed after drawing the first strand attached to magnetic beads to the side of the tube with the use of a magnet. PCR was performed using 2 µl second strand cDNA, 200 nM of each primer, 2 µM dNTPs, 0.2 µl $\alpha\text{-}[^{33}P]dATP$ (2,000 Ci/mmole), 100 mM Tris-HCl (pH 8.4), 50 mM KCl, 1.5 mM $MgCl_2$, 0.001% w/v gelatin and 1 unit Taq DNA polymerase (Qiagen) in a 20 µl reaction. Amplification was carried out in a Perkin Elmer 9700 DNA thermal cycler for 40 cycles of denaturation at 94° C. for 30 seconds, annealling at 40° C. for 2 minutes and extension at 72° C. for one minute, with a final extension at 72° C. for 5 minutes. The PCR products were separated on a 4.5% w/v polyacrylamide gel and differentially expressed PCR fragments were visualized by exposing the dried gel to x-ray film.

EXAMPLE 6

Band Recovery, Cloning and Sequencing

Candidate bands were excised from the gel and reamplified by PCR using the appropriate primer combination under the PCR conditions stated above except that the dNTP condition was 20 µM and no radioisotope was included. The putative differentially expressed cDNA fragments were cloned using the pCR-TRAP cloning system (GenHunter Corporation). Sequencing reactions were carried out using ABI PRISM dye terminator cycle sequencing ready reaction kits and analysed on an ABI 373A DNA sequencer. Gene database searches were performed at the National Centre for Biotechnology Information using the BLAST network service.

EXAMPLE 7

Quantitation of Gene Expression

Animals were killed by lethal overdose of pentobarbitone (120 mg/kg) and the following tissues were removed: liver, spleen, kidney, heart, skeletal muscle (gastrocnemius), and adipose tissue from the suprascapular, perirenal, intramuscular and mesenteric fat depots. RNA was extracted from tissues using RNEasy kits (Qiagen, Hilden, Germany). RNA was quantitated by spectrophotometry at 260 nm, and 1 μg of RNA was then reverse transcribed at 42° C. for 1 h with 10 U of AMV Reverse Transcriptase (Boehringer Mannheim, Mannheim, Germany) according to the manufacturer's instructions. Oligonucleotide primers for the beacon gene PCR were chosen from the sequence previously determined. Primers were also selected for the beta-actin gene by comparing mRNA sequences from various mammals to identify highly conserved regions. The primer sequences used were:

```
beta-ac-  forward
tin-
          5'-agtccgcgttaagtgcaaca-3' [SEQ ID NO: 6]

reverse
          5'-ctccaggttcatcccatcgt-3' [SEQ ID NO: 7]

beacon-   forward
          5'-ggctacagcttcaccaccac-3' [SEQ ID NO: 8]

reverse
          5'-gcttgctgatccacatctgc-3' [SEQ ID NO: 9]
```

PCR was performed by adding 100 ng of cDNA to a reaction mix containing 10 mM Tris-HCl (pH 8.3 at 20° C.), 1.5 mM $MgCl_2$, 50 mM KCl, 200 μM each dNTP, 100 pmol each primer and 1.25 U Taq DNA Polymerase (Qiagen). Standard PCR consisted of 30 cycles of 94° C. for 0.5 min (denaturation), 58° C. (beta-actin) or 53° C. (beacon) for 0.5 min (annealing) and 72° C. for 1 min (extension), with a final extension step of 72° C. for 5 min. 10 μl of each PCR product was fractionated by agarose gel electrophoresis in a 2% w/v gel containing 0.5 μg/ml ethidium bromide at 6 V/cm for 90 min and photographed under ultraviolet transillumination at 302 nm. For quantitation of beacon gene expression, the linear phases of both of the above PCR's were determined empirically as 20 cycles for beta-actin and 24 cycles for beacon. PCR's and electrophoresis were conducted as above (for the appropriate number of cycles) and gene expression quantitated by computerized densitometry (Eagle Eye II System, Stratagene, USA). beacon gene expression was determined as the ratio of densities of beacon to beta-actin PCR products from the same tissues.

EXAMPLE 8

Statistical Analysis

All experimental data are expressed as means ± s.e.m. A one-way analysis of variance in combination with a Tukey's multiple comparison test was used to compare means between and within groups, and a two-sample unpaired t-test was used where appropriate. In all instances probability values of <0.05 were considered significant.

EXAMPLE 9

Identification of a Body Weight-related Gene by ddPCR

To identify novel genes that are associated with regulation of energy balance, we compared the hypothalamic mRNA profile of lean and obese *Psammomys obesus*. One cDNA fragment amplified with the G-anchored primer and arbitrary primer 11 was found to be expressed in larger amounts in the obese animals. The cDNA band of approximately 400 base pairs was excised from the gel, reamplified and cloned.

EXAMPLE 10

Nucleotide Sequence

Figure 1A:
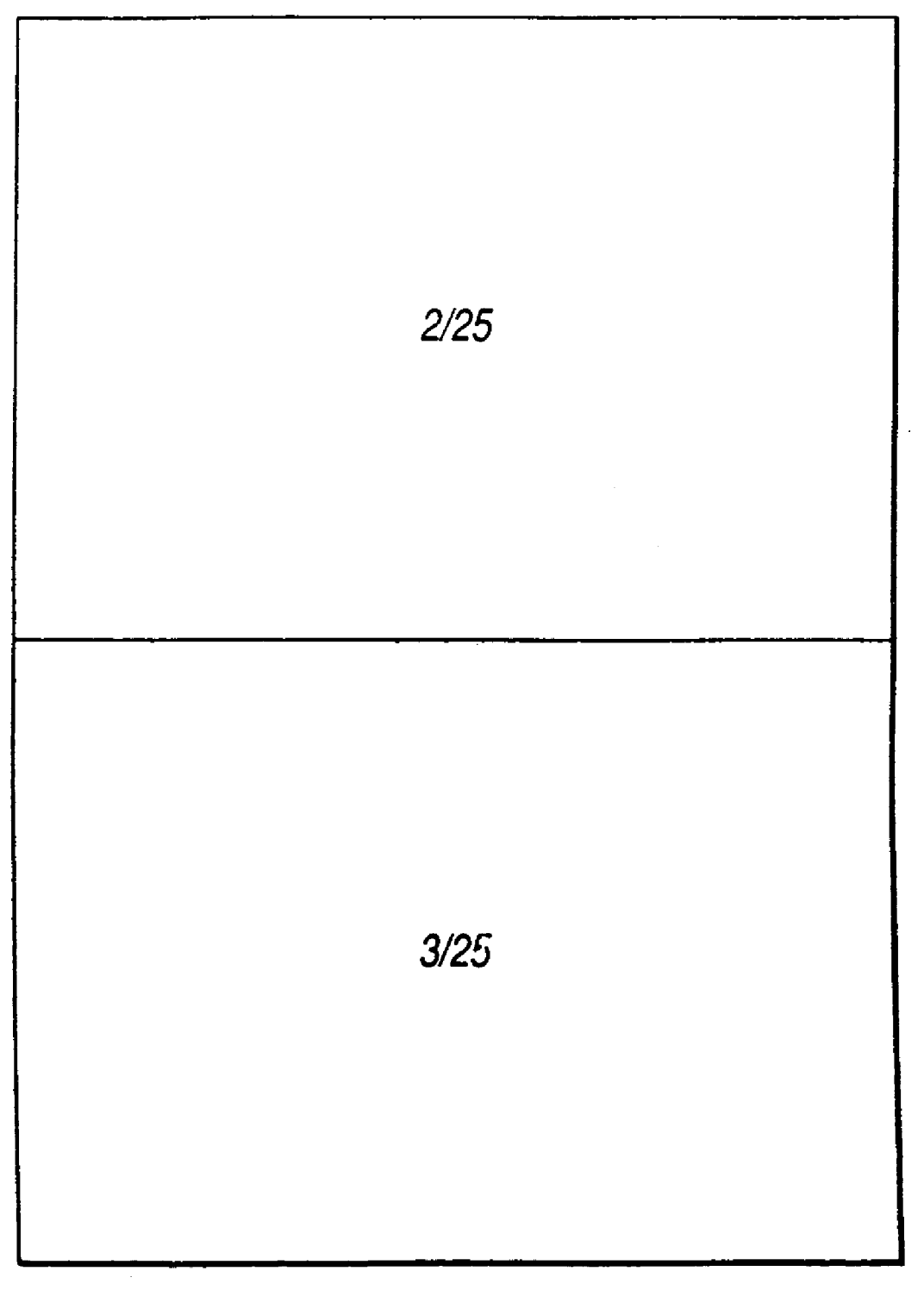

Both strands of the differentially expressed band from the obese animals were sequenced. The sequences were identical and are shown in FIG. 1A the coding sequence is SEQ ID NO:1 and the complementary sequence is SEQ ID NO:3. The corresponding amino acid sequence is SEQ ID NO:2. This sequence was compared against nucleotide sequence databases and the six-frame conceptual translation products against protein sequence databases. Strong homology was found with genes from humans, mice, *Caenorhabditis elegans, Fasciola hepatica*, rice and *Saccharomyces cerevisiae* and weaker homology with ubiquitin and ubiquitin-like proteins. The genes in other species were not named, the inventors called the gene beacon. The translation product of the *C. elegans* gene denoted as 'weak similarity to *Arabidopsis thaliana* ubiquitin-like protein 8' was 81% homologous with beacon and enabled the open reading frame of beacon to be determined. Beacon was found to be 73 amino acids long, the same length as the *C. elegans* gene. Both the start and stop codons were identified within the ddPCR fragment, eliminating the need to probe a cDNA library to determine the full sequence. The full amino acid sequence of beacon is shown in FIG. 1 and the amino acid alignments with gene products in humans, mice, *C. elegans, F. hepatica*, rice and *S. cerevisiae*, and also human ubiquitin and ubiquitin-like protein 8 from *Arabidopsis thaliana* are shown in FIGS. 2A and B.

The nucleotide sequence and corresponding amino acid sequence for human beacon shown in FIG. 1B and corresponds to SEQ ID NO:13 and 14, respectively. The human beacon sequence substantially corresponds to a short form of the *Psammomys obesus* with the exception that amino acid 15 may be His or Arg and the corresponding codon is CAC or CGC, respectively. In FIG. 1B this codon is represented as "CNC" wherein N is preferably A or G.

EXAMPLE 11

Analysis of Protein

Analysis of the putative protein sequence using ProtParam tool indicated that beacon has a molecular weight of 8503.9 and is a stable protein with an estimated half-life of 30 hours. The protein does not have an aminoterminal signal sequence often found in proteins destined for export from the cell or for a membrane location. No nuclear targeting signal was found suggesting that beacon is not found in the nucleus. Transmembrane segments were also not found, but beacon may be a peripheral membrane protein, binding to the surface of integral membrane proteins. Beacon appears to have an intramitochondrial signal and may be located within the mitochondrial intermembrane space or the mitochondrial matrix space. Many proteins localized at the mitochondrial inner membrane are likely to be peripheral membrane proteins which exist as members of large membrane complexes. A short form of beacon (33 amino acids) is used in some of the studies. Preliminary human sequence data for beacon indicate that in humans, a premature stop codon results in the 33 amino acid short form. The short form comprises the first 33 amino acids of the amino acid sequence given in FIGS. 1B and 2A for human beacon. Amino acid 15 of human beacon may be His or Arg. The short form is also easier to synthesize chemically.

EXAMPLE 12

PCR of the Beacon Gene

PCR primers were designed from the nucleotide sequence of beacon to yield a PCR product of 169 bp. These primers successfully yielded the correct size PCR product with *Psammomys obesus* hypothalamic cDNA. PCR of *Psammomys obesus* genomic DNA yielded the same size product also, indicating that there are no introns within the gene. PCR was also performed on human genomic DNA and the same size product was detected, confirming that the beacon gene is also found in humans.

EXAMPLE 13

Tissue Distribution of Beacon Gene Expression in *Psammomys obesus*

The beacon gene was expressed at significant levels in all tissues tested in *Psammomys obesus* (hypothalamus, liver, adipose tissue, skeletal muscle (gastrocnemius), heart, pancreas, kidney and spleen).

EXAMPLE 14

Hypothalamic Beacon Gene Expression

Figure 3A:
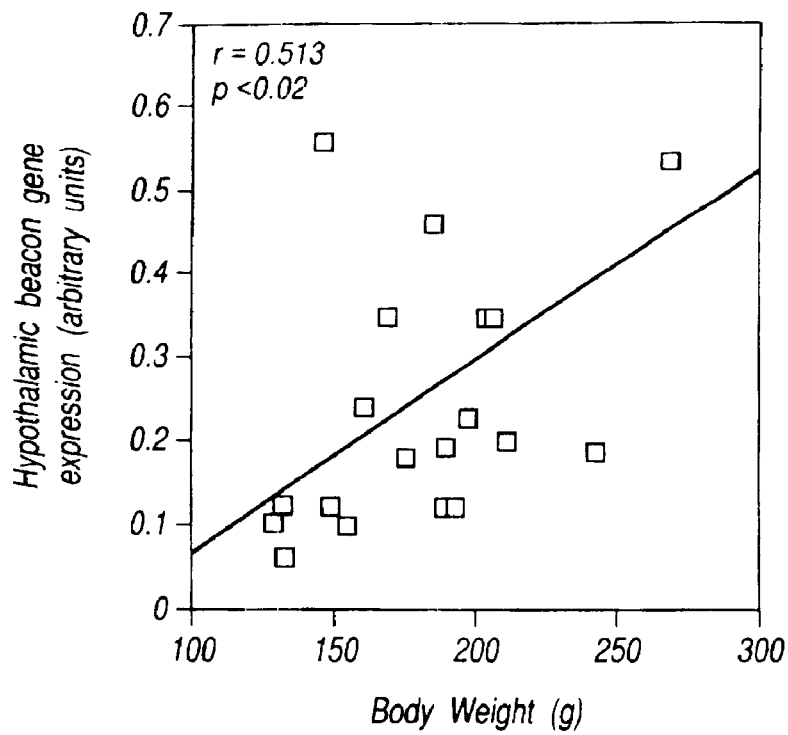
FIG. 3 is a graphical representation showing correlations of hypothalamic beacon gene expression with (A) body weight and (B) log plasma insulin concentrations in Psammomys obesus.
Figure 3B:
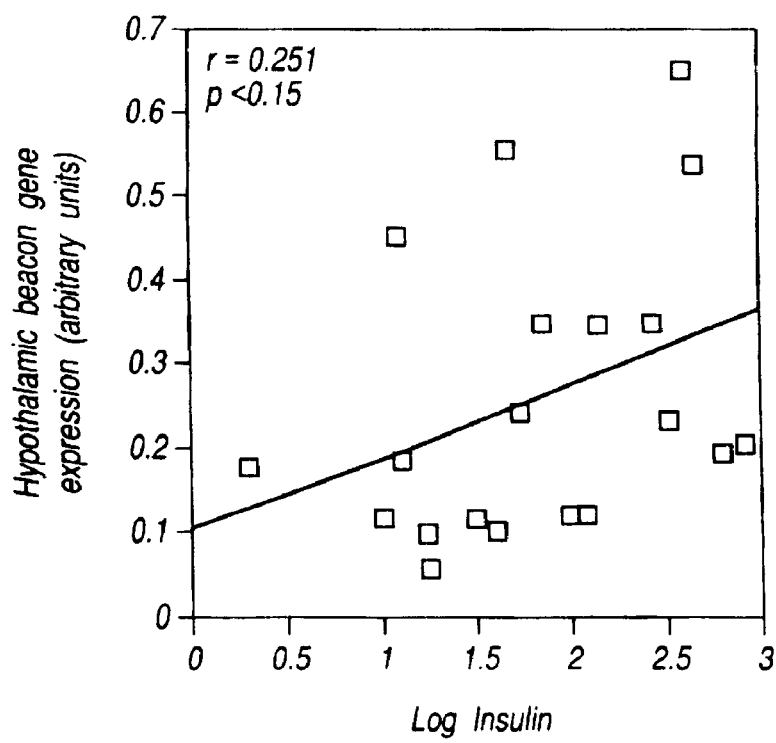
Figure 4A:
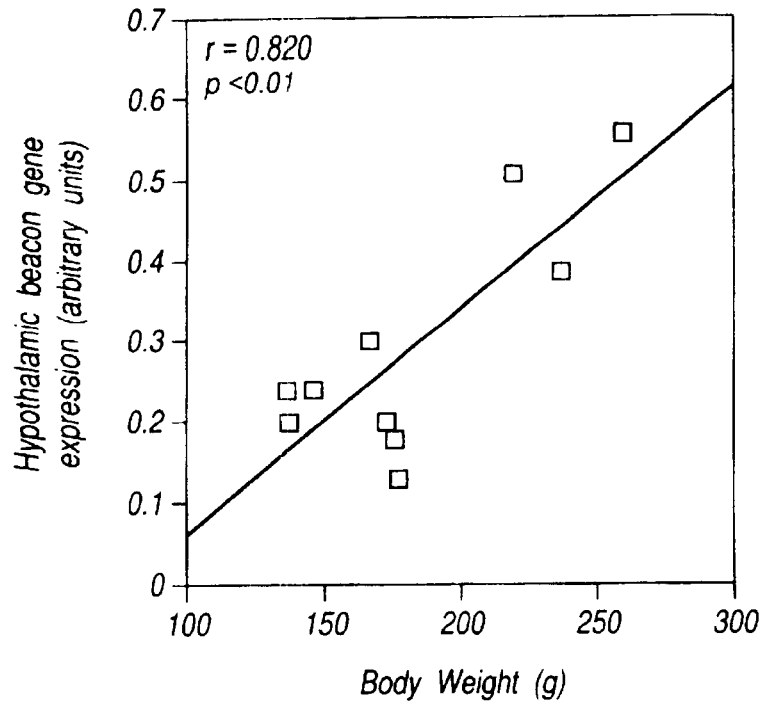
FIG. 4 is a graphical representation showing improved correlations of hypothalamic beacon gene expression with (A) body weight and (B) log plasma insulin concentrations in leptin-treated Psammomys obesus.
Figure 4B:
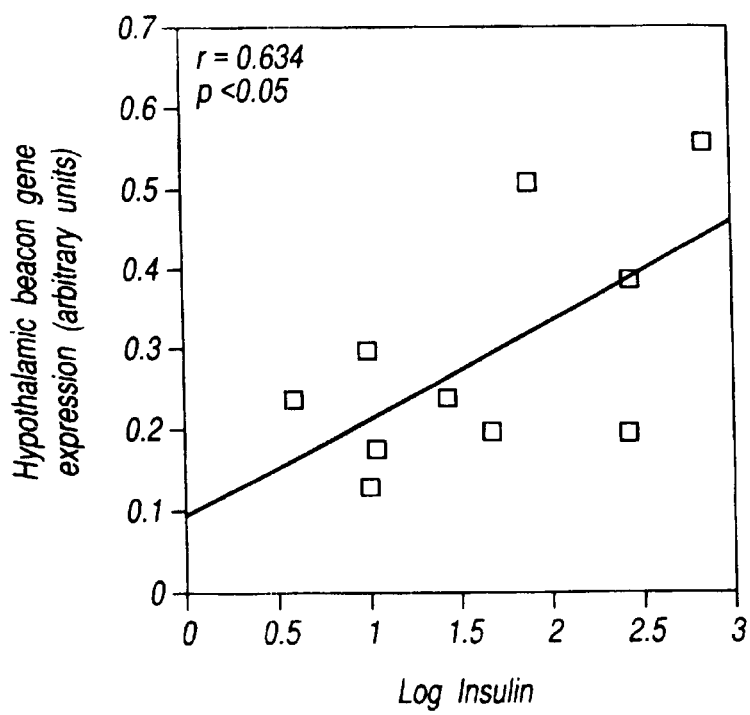
Figure 5A:
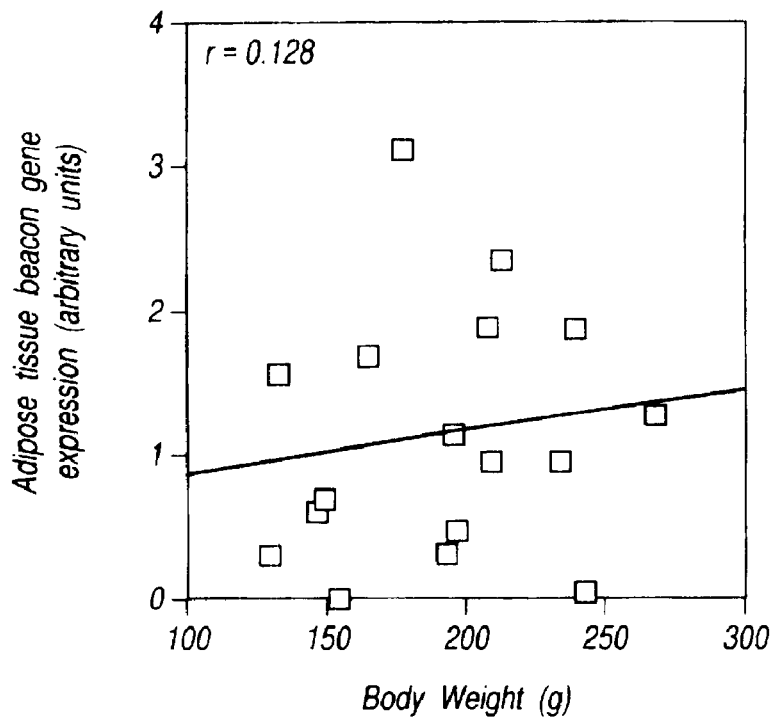
FIG. 5 is a graphical representation showing correlations of beacon gene expression in adipose tissue with (A) body weight and (B) log plasma insulin, and in liver with (C) body weight and (D) log plasma insulin.
Figure 5B:
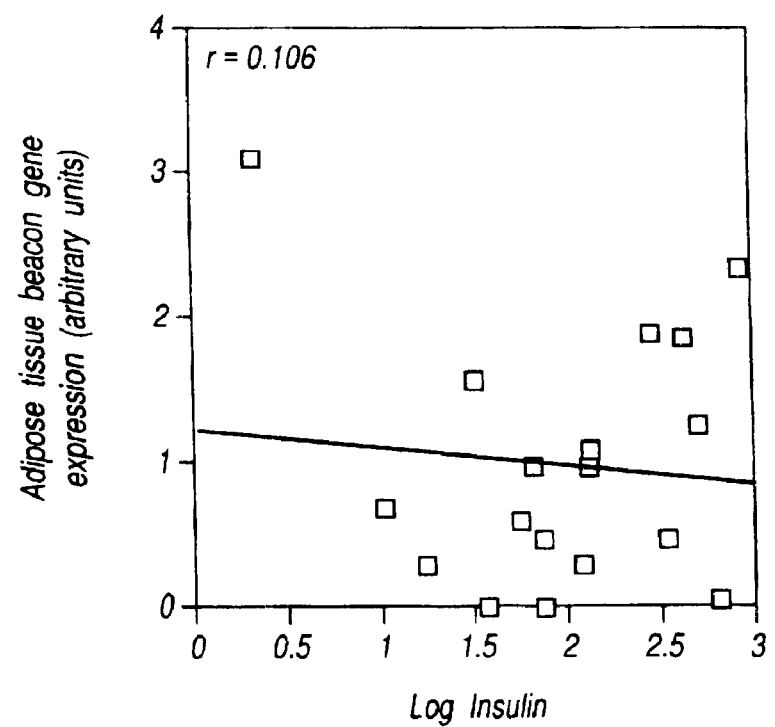
Figure 5C:
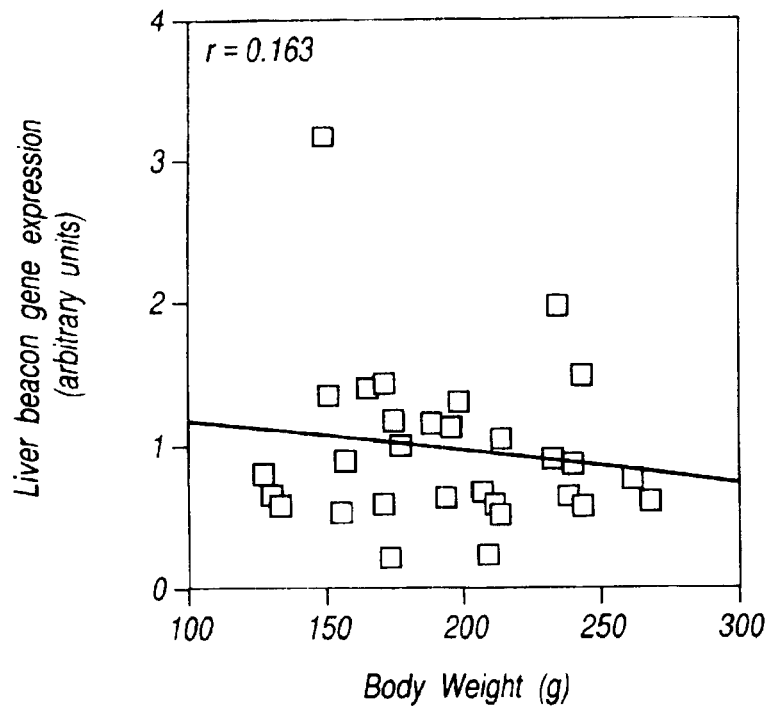
Figure 5D:
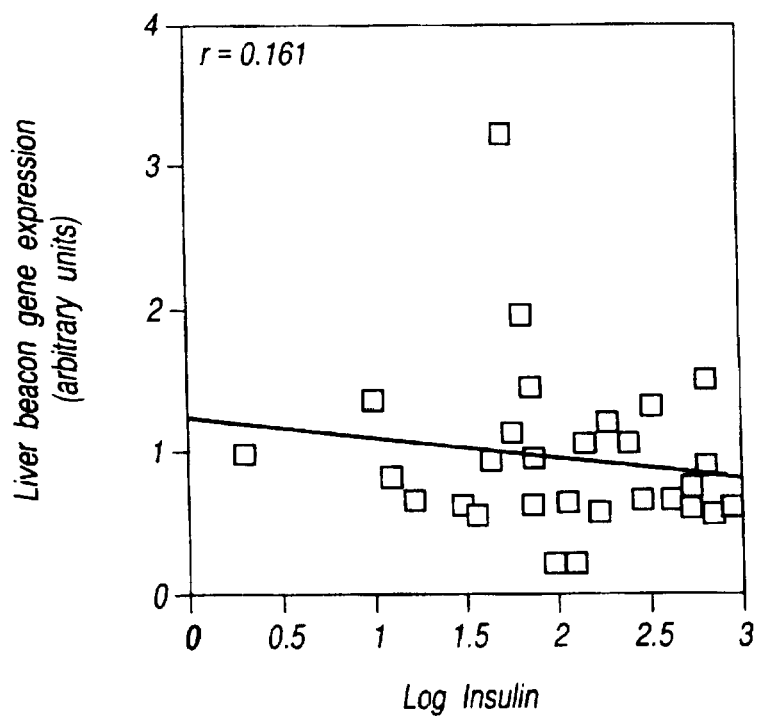

Hypothalamic expression of the beacon gene was significantly correlated with body weight and plasma insulin concentrations in *Psammomys obesus* (FIG. 3). Correlation coefficients of beacon gene expression with body weight and plasma insulin were all markedly improved after six days of leptin administration (FIG. 4). Neither Adipose tissue beacon gene expression or liver beacon gene expression were significantly correlated with body weight or circulating insulin levels (FIG. 5). Expression of beacon was not related to obesity in tissues other than the hypothalamus.

EXAMPLE 15

Leptin Treatment

Figure 6:
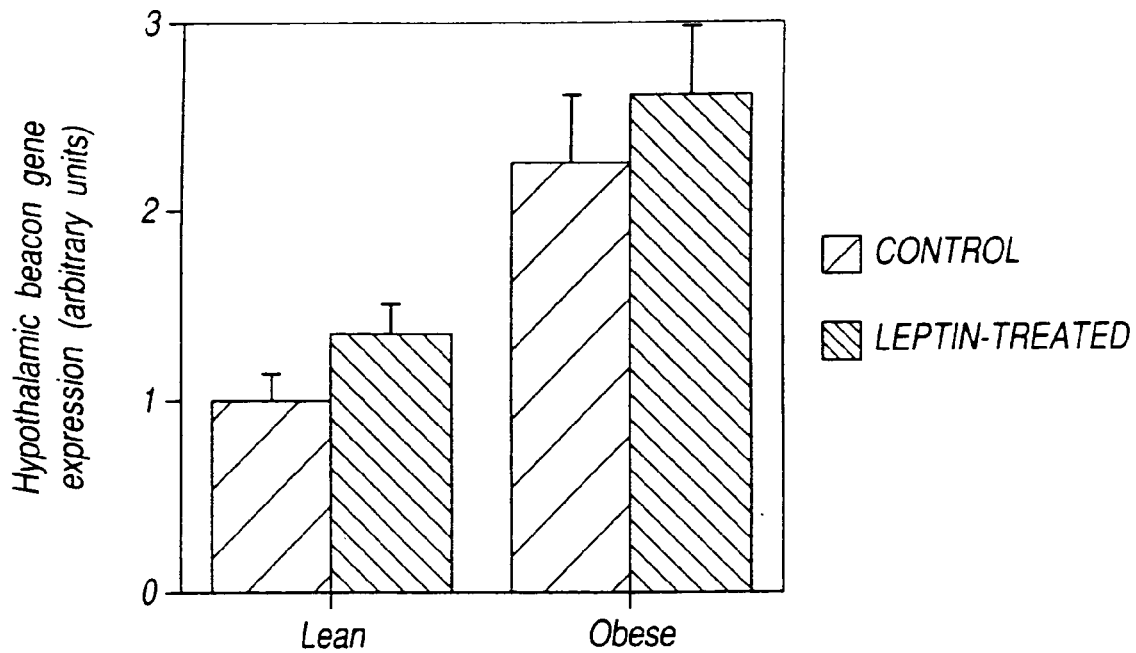
FIG. 6 is a graphical representation showing effects of leptin treatment on hypothalamic beacon gene expression in lean and obese Psammomys obesus.
Figure 7:
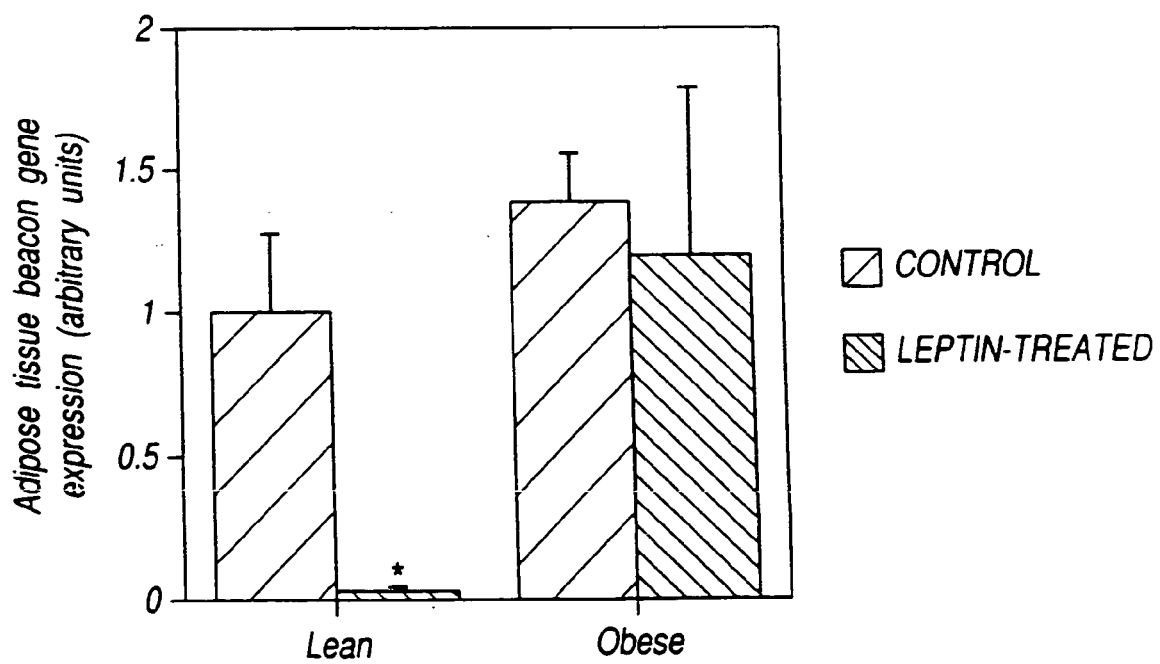
FIG. 7 is a graphical representation showing effects of leptin treatment on adipose tissue beacon gene expression in lean and obese Psammomys obesus. (*p=0.014 compared with lean control animals).

Leptin treatment resulted in an increase in beacon gene expression in the hypothalamus of the group A, lean animals but no difference in the obese group B animals (FIG. 6). In contrast beacon gene expression in adipose tissue was significantly reduced following leptin treatment in lean animals and similarly unchanged in leptin resistant obese group B animals (FIG. 7).

EXAMPLE 16

Nicotine Treatment

Figure 8A:
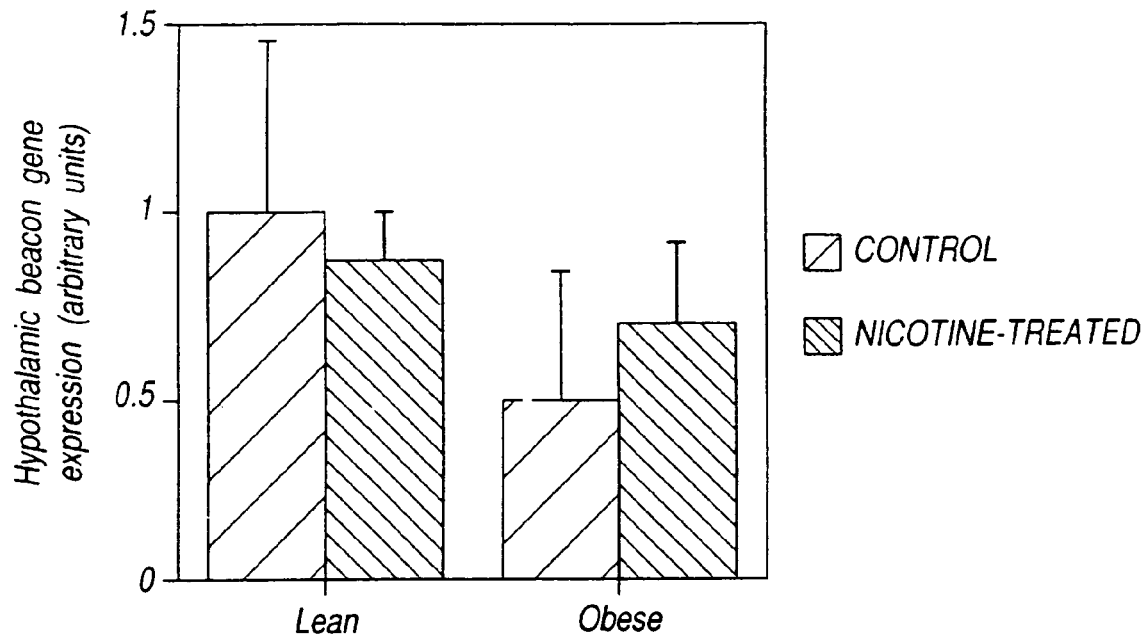
FIG. 8 is a graphical representation showing effects of nicotine treatment on (A) hypothalamic and (B) adipose tissue beacon gene expression in lean and obese Psammomys obesus.
Figure 8B:
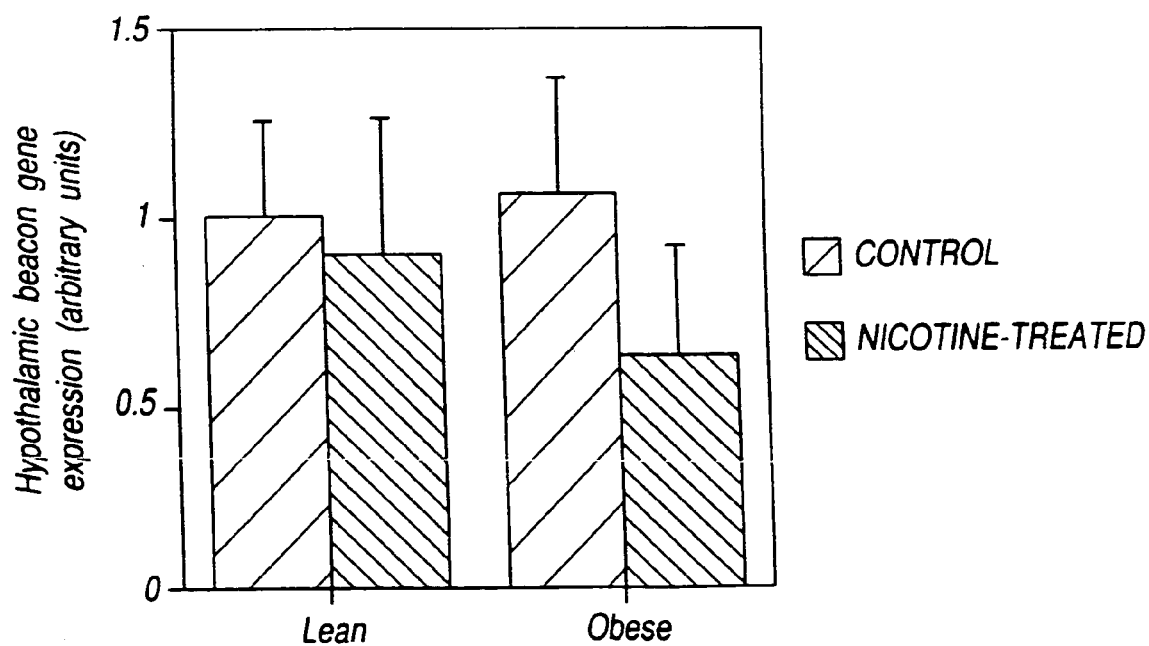

Nicotine treatment failed to have any effects on beacon gene expression in either hypothalamus or adipose tissue despite significant effects of nicotine treatment on body weight and food intake (FIG. 8). These results suggest the effects of leptin treatment on beacon gene expression are in fact, independent of body weight and leptin specific.

EXAMPLE 17

Chronic Beacon Studies

Chronic studies were conducted on three groups of *Psammomys obesus*.

The *Psammomys obesus* colony can be classified into three groups based on their blood glucose and insulin levels at 12 weeks of age in the fed state (Barnett et al, 1994a). In essence, Group A is a lean group of animals, Group B is an obese, non-diabetic group of animals and Group C is an obese, diabetic group of animals.

| GROUP A: | NORMOGLYCEMIC | Glucose | $\leq 8$ mM |
| | NORMOINSULINEMIC | Insulin | $\leq 150$ mU/mL |
| GROUP B: | NORMOGLYCEMIC | Glucose | $\leq 8$ mM |
| | HYPERINSULINEMIC | Insulin | $>150$ mU/mL |
| GROUP C: | HYPERGLYCEMIC | Glucose | $>8$ mM |
| | HYPERINSULINEMIC | Insulin | $>150$ mU/ml |

When compared to normoglycemic and normoinsulinemic Group A animals, Group C *Psammomys obesus* develop a number of abnormalities including hyperglycemia, hyperinsulinemia, increased fat stores, body weight, elevated triglyceride and cholesterol levels and hyperleptinemia (Barnett et al, 1994b). These changes represent some of the key features of the metabolic syndrome or Syndrome X.

Previous studies have shown that individual animals may progress around the curve in a clockwise direction, from Group A to B to C (Shafir and Gutman, 1993). However the metabolic and physical abnormalities demonstrated in obese Group C *Psammomys obesus* may be corrected by dietary manipulation. Dietary restriction significantly reduces body weight, blood glucose and plasma insulin concentrations (Barnett et al, 1994a).

Animals (27 animals total) with ICV cannulas and Alzet pumps were chronically infused with the chemically synthesised short form of beacon (33 amino acids in length, dose=15 ug/day) whilst control animals (28 animals total) were infused with saline. A separate group of animals were treated with neuropeptide Y which is known to increase body weight and food intake. The pumps are designed to deliver solution for 7 days and body weight and food intake were monitored on a daily basis over this time period.

Figure 9A:
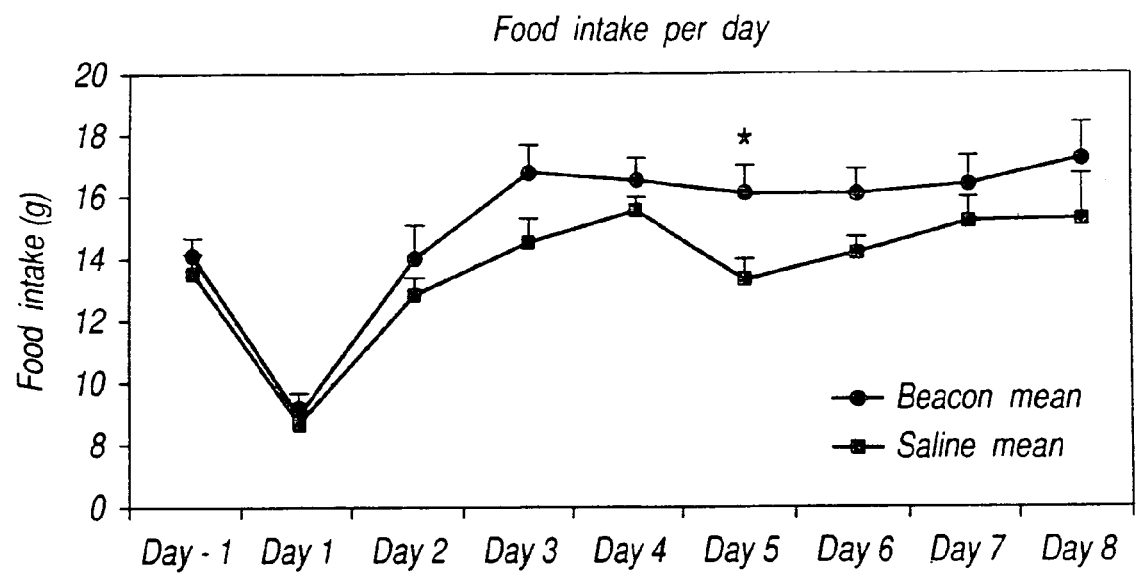
FIG. 9 is a graphical representation of (A) food intake per day; (B) cumulative food intake; and (C) body weight change in Psammomys obesus over an 8 day period administered with beacon or saline.
Figure 9B:
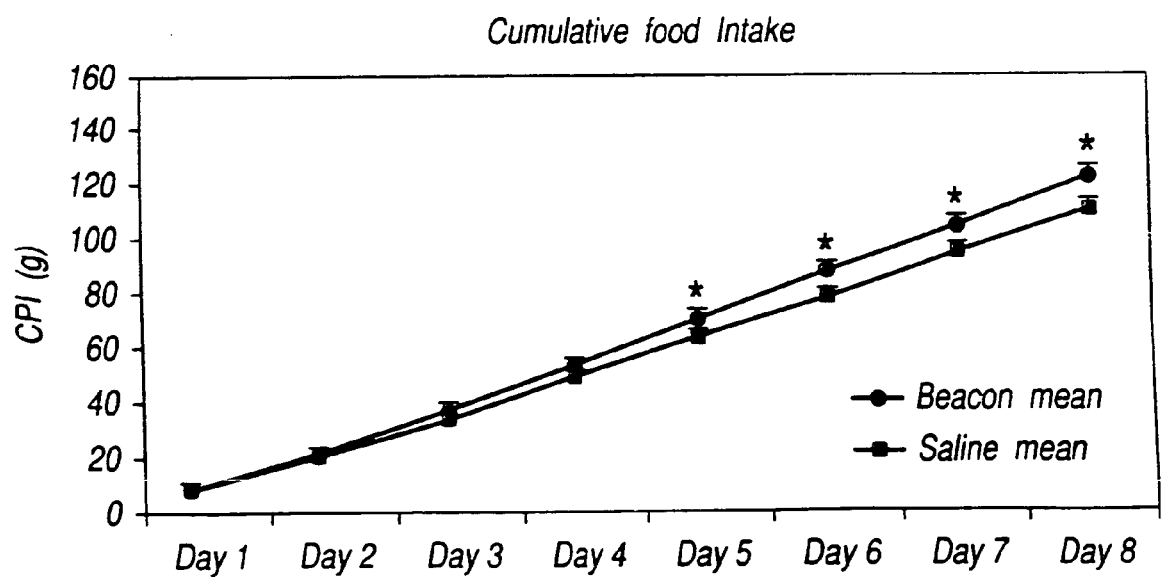
Figure 9C:
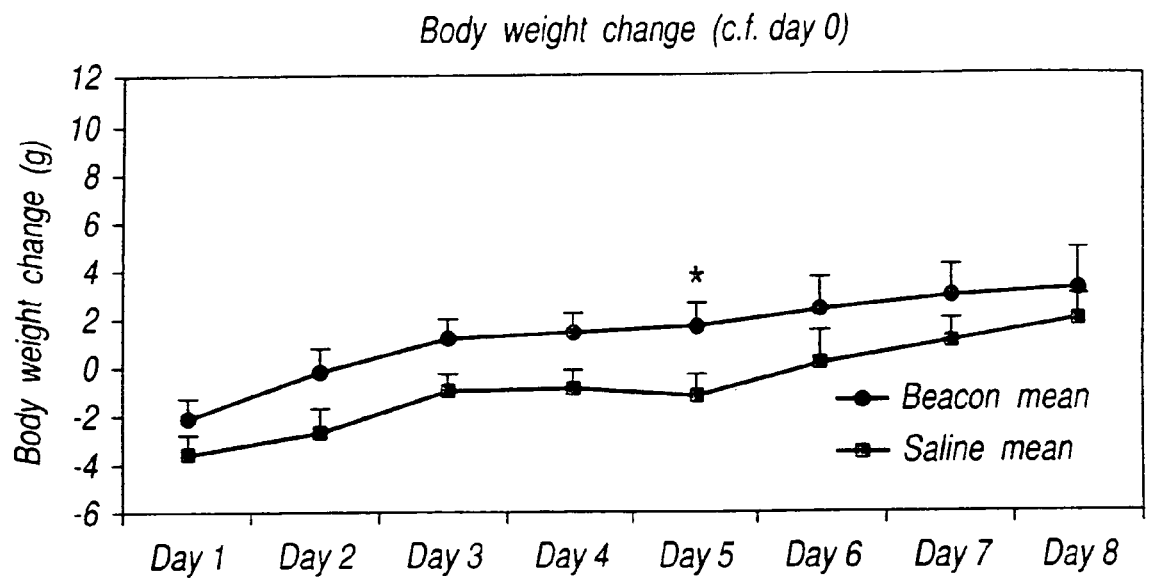
Figure 10A:
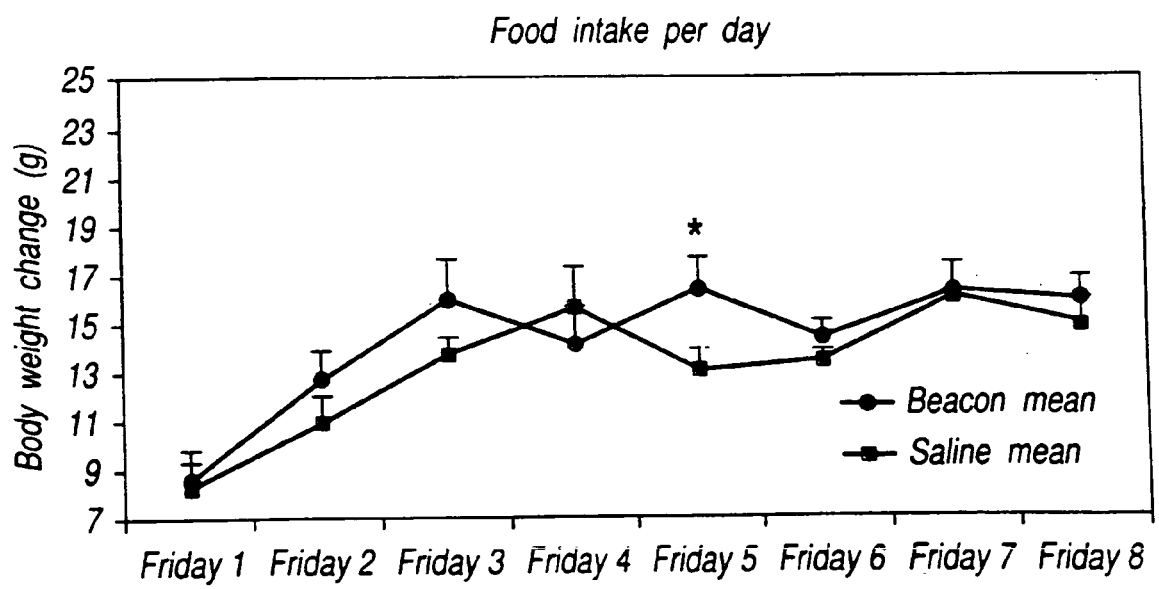
FIG. 10 is a graphical representation showing food intake per day in (A) Group A Psammomys obesus; (B) Group B Psammomys obesus and (C) Group C Psammomys obesus administered with beacon or saline.
Figure 10B:
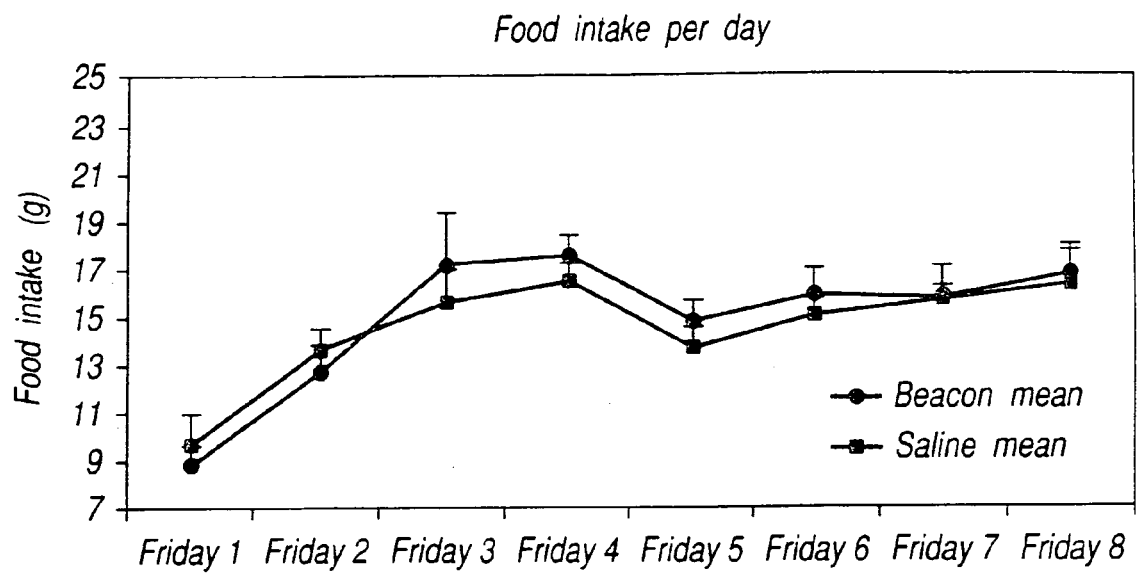
Figure 10C:
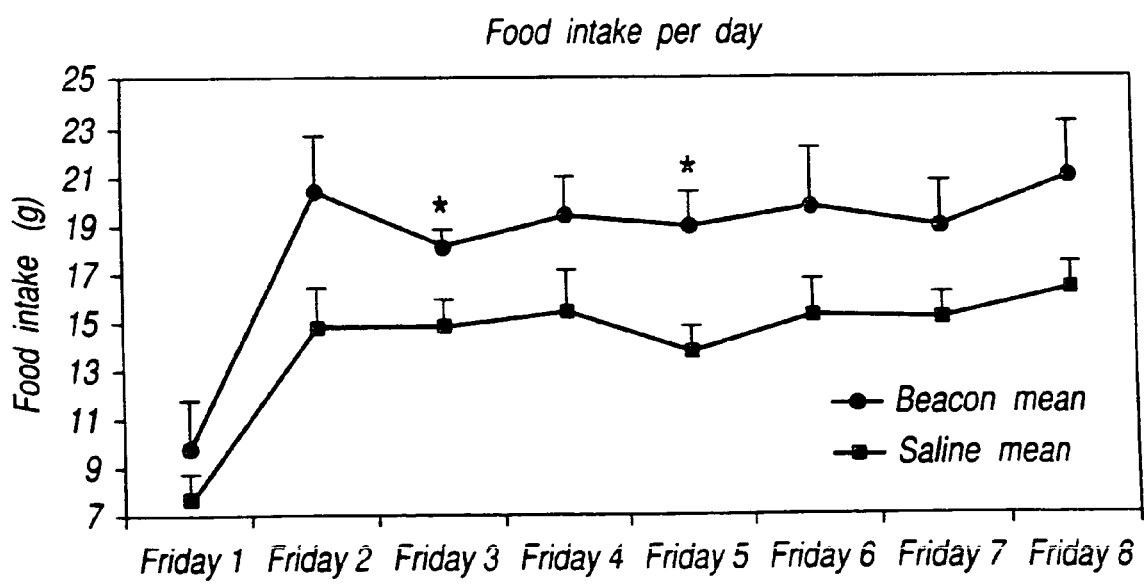
Figure 11A:
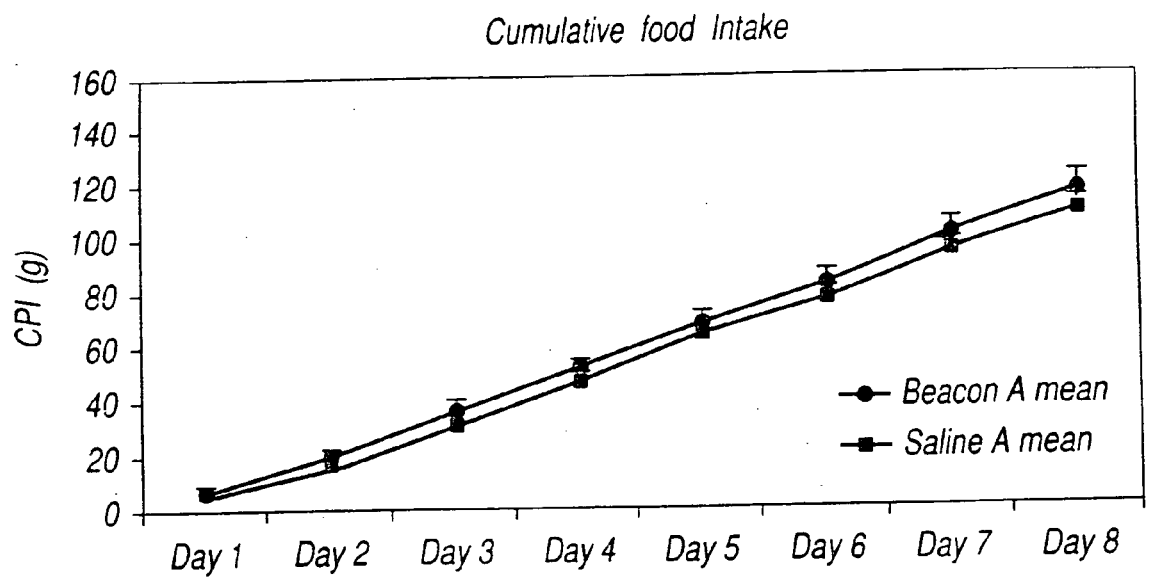
FIG. 11 is a graphical representation showing cumulative food intake over a 8 day period in (A) Group A Psammomys obesus; (B) Group B Psammomys obesus; and (C) Group C Psammomys obesus administered with beacon or saline.
Figure 11B:
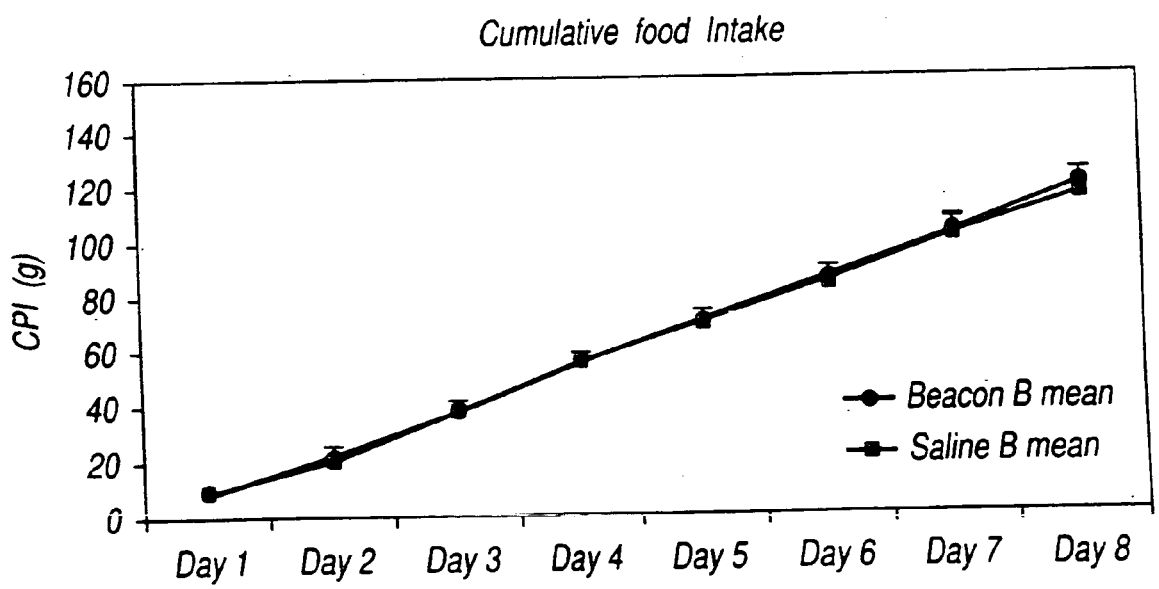
Figure 11C:
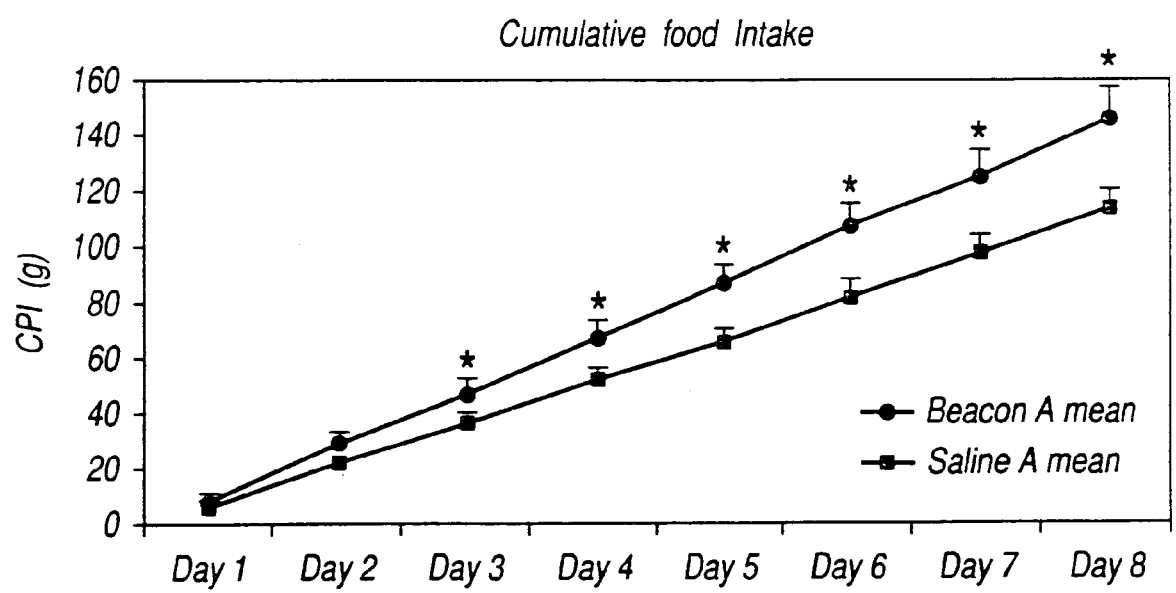

The results are shown in FIGS. 9-11. FIGS. 9A-C show a comparison between beacon and saline administration to *Psammomys obesus* as monitored by food intake, cumulative food intake and body weight change. FIGS. 10A-C show food intake per day for Group A, B and C *Psammomys obesus* administered with beacon or saline. FIGS. 11A-C show cumulative food intake for Group A, B and C *Psammomys obesus* administered with beacon or saline.

The chronic studies indicate that beacon acts in a similar fashion to neuropeptide Y by increasing food intake and body weight. Over the 7-day treatment period of the Alzet pump, food intake/day was increased in beacon treated animals compared to saline controls with a maximal increase (~20%) at day 5. Similarly, cumulative food intake and body weight was greater in the beacon treated animals compared to saline controls.

When the animals are divided into groups of A, B and C, it is observed that the increases in body weight and food intake following beacon treatment are more pronounced in the C (n=7_animals. There was little difference in body weight and food intake for beacon treated A (n=9) or B (n=13) animals compared to saline treated B animals (n=13).

EXAMPLE 18

Beacon Gene Expression

Figure 12A:
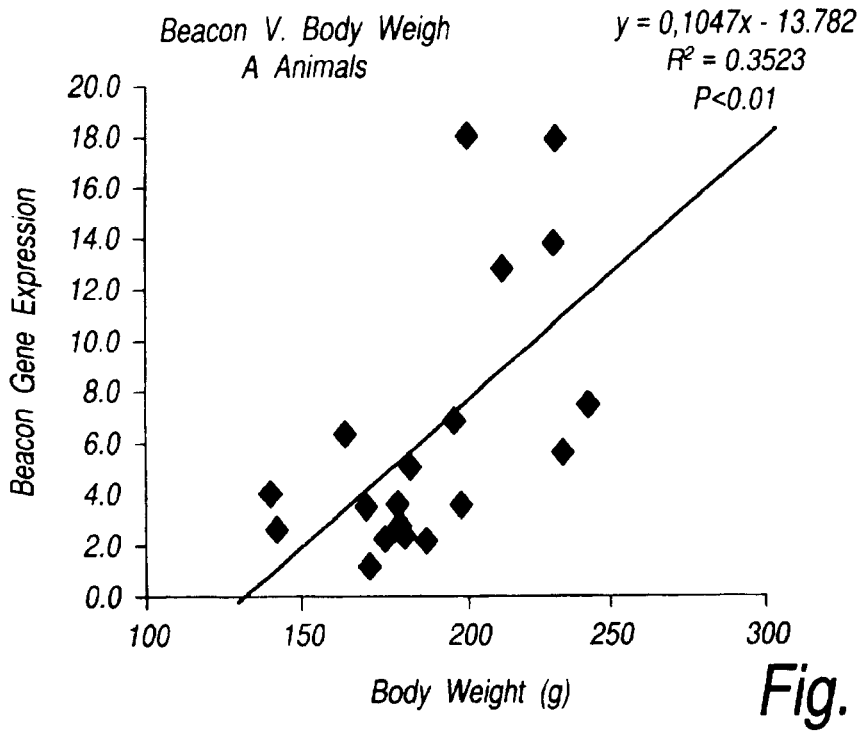
FIG. 12 is a graphical representation showing beacon gene expression verses (A) body weight; and (B) percentage body fat in Group A Psammomys obesus.
Figure 12B:
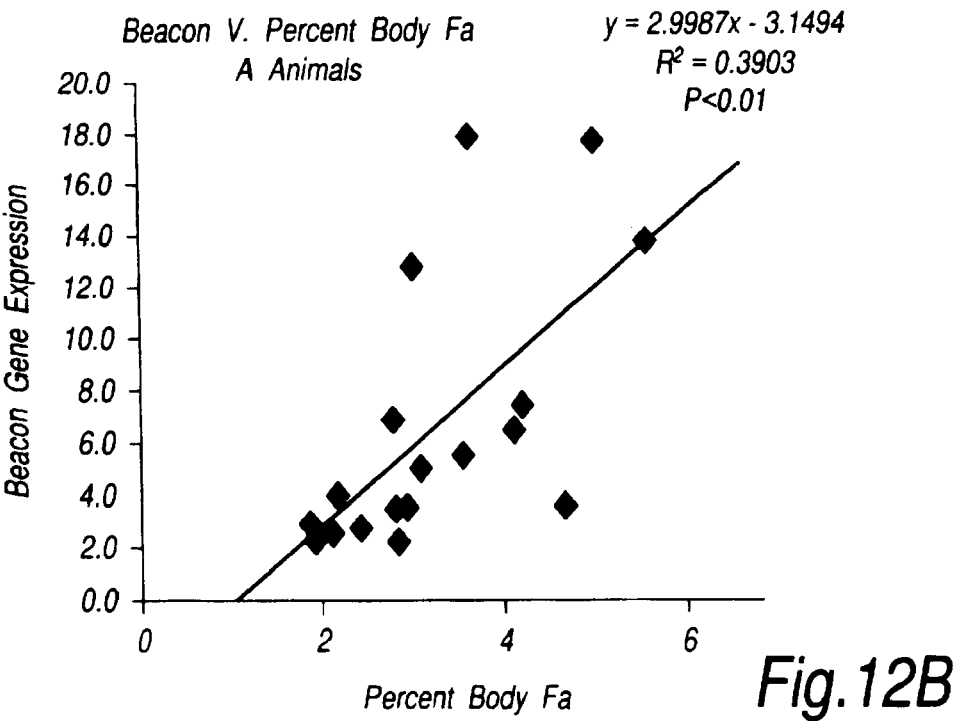
Figure 13A:
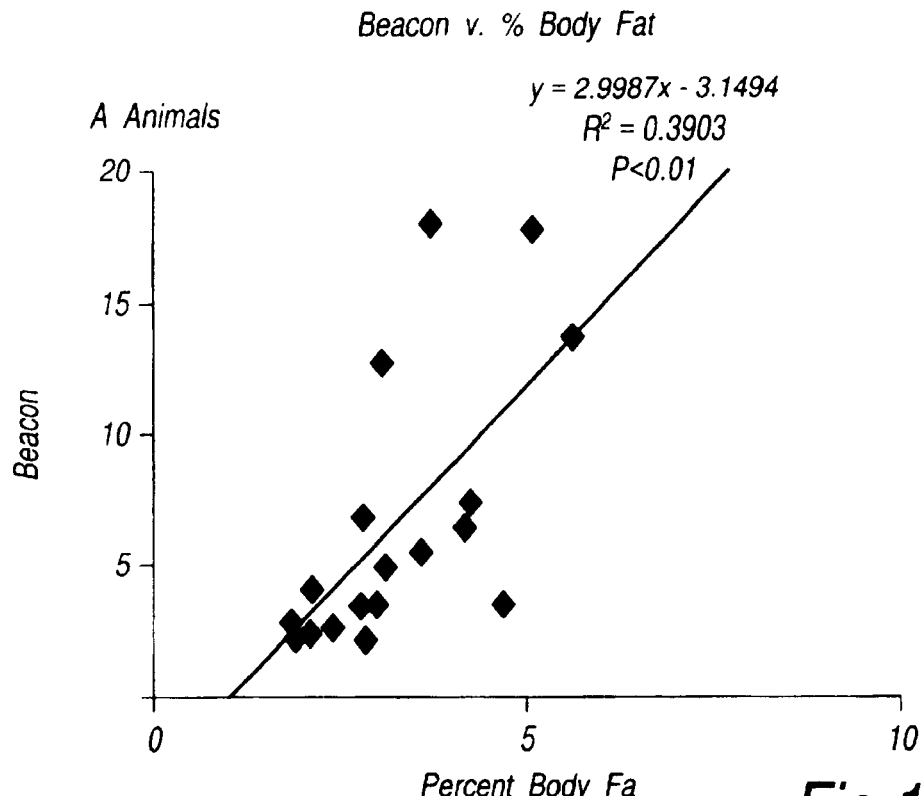
FIG. 13 is a graphical representation showing beacon gene expression verses percentage body fat in (A) Group A Psammomys obesus; (B) Group B Psammomys obesus; and (C) Group C Psammomys obesus.
Figure 13B:
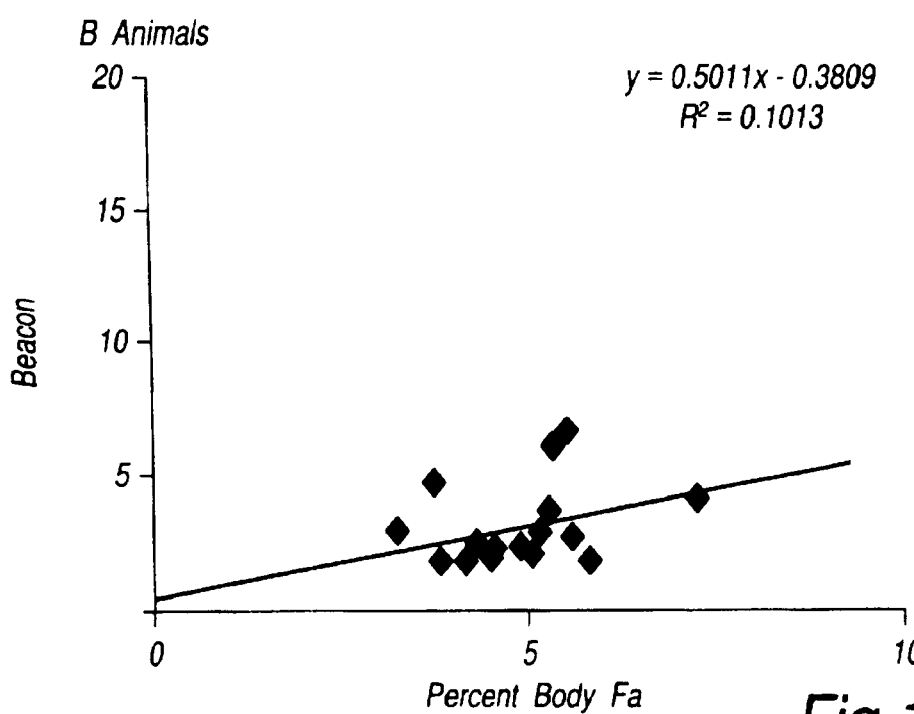

Studies were conducted to monitor the effects of expression of the beacon gene in *P. obesus Psammomys obesus*. The results are shown in FIGS. 12 to 14. The expression of beacon increases in all Group A, B and C *Psammomys obesus* with increased body weight or percentage body fat (FIGS. 12 and 13). Group A animals expressed the highest level of beacon (FIG. 14) compared to Group B and C animals. These gene expression studies were conducted using a Perkin Elmer "Real-Time" PCR as described below.

Real time PCR performed on the ABI Prism 7700 Sequence Detector system consists of a fluorescent-labelled target probe and forward and reverse primers, all of which are specific for the target sequence. The probe is labelled at the 5' end with a reporter dye and at the 3' end with a quencher dye and while the probe is intact the proximity of the quencher reduces the fluorescence emitted by the reporter. The probe anneals downstream from one of the primer sites and as the PCR progresses, the 5' nuclease activity of Taq DNA polymerase cleaves the reporter dye from the probe. Once separated from the quencher, the reporter dye emits a characteristic fluorescence.

The ABI Prism 7700 Sequence Detector has a built-in thermal cycler and a laser directed via fibre optic cables to each of 96 sample wells. Fluorescence emission data produced during PCR is collected once every few seconds and travels back to the CCD camera detector. Software within the Sequence Detector system analyses the data and amplification plots are produced for each sample allowing us to monitor the entire PCR process for amplification of any specific target sequence. Reactions are categorised by the point in time during cycling when amplification of a product is first detected rather than the amount of product formed after a fixed number of cycles. The higher the amount of target starting material, the sooner a significant increase in fluorescence will be observed.

The probe and primer sequences used for the beacon gene expression studies are shown below;

```
                                        [SEQ ID NO: 10]
Probe      6FAM-TGGTAATAAAGCTCCAGGTTCATCCCATCG-TAMRA (6FAM = fluorescent reporter dye and
           TAMRA = quencher dye)

[SEQ ID NO: 11]
Forward    CAAACTGGCACTCGTTGGAA
Primer

[SEQ ID NO: 12]
Reverse    GTTGGGCAAGGTGGAGGAA
Primer
```

EXAMPLE 19

Effects of Insulin on Beacon Gene Expression

Figure 15:
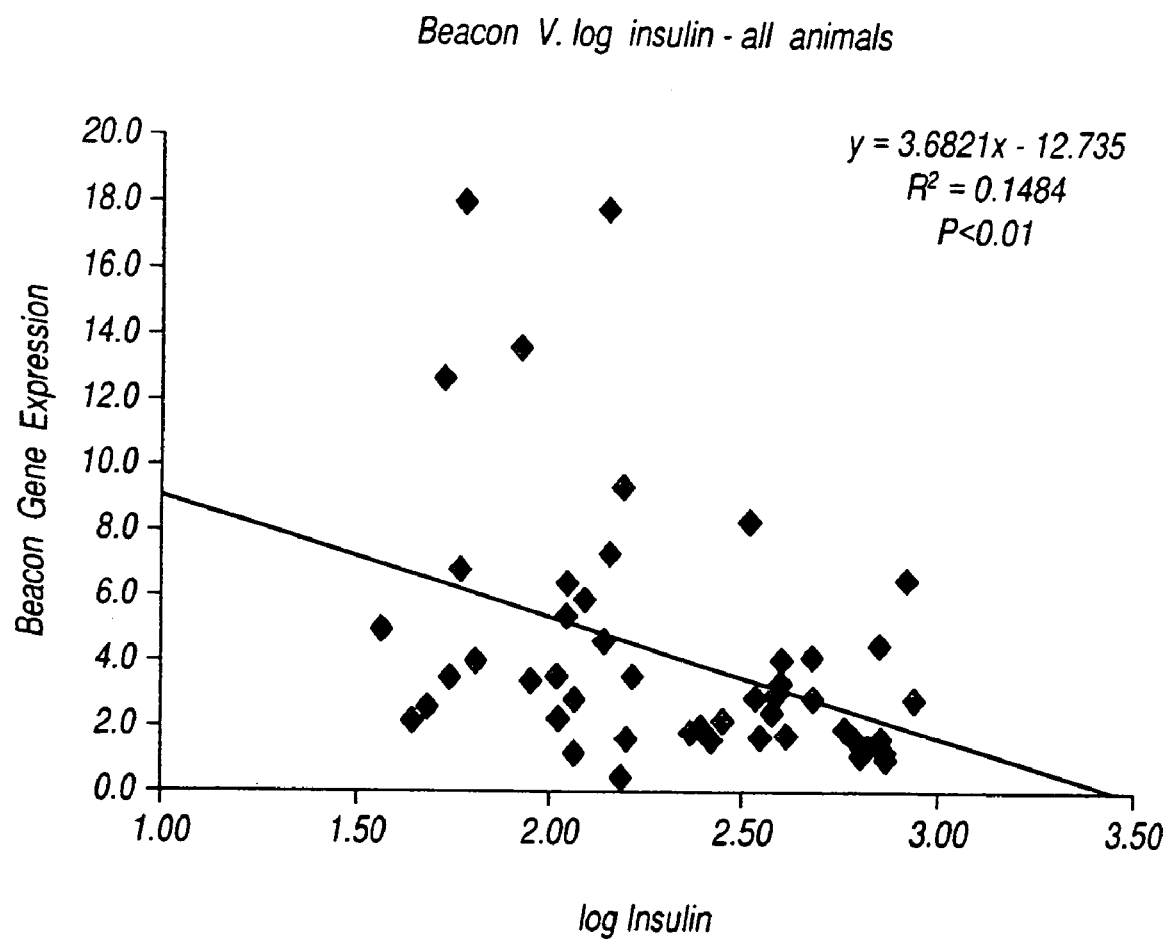
FIG. 15 is a graphical representation showing beacon gene expression verses log insulin in Group A, B and C Psammomys obesus animals.

The effects of insulin on beacon gene expression are shown in FIG. 15. The data show that increasing levels of insulin results in a decrease in beacon gene expression. These results show that beacon gene expression is affected in metabolically disturbed animals and insulin retards beacon expression.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Barnett M, Collier G R, Collier F M, Zimmet P, O'Dea K (1994a) A cross-sectional and short-term longitudinal characterisation of NIDDM in *Psammomys obesus*. *Diabetologia* 37: 671-676.

Barnett M, Collier G R, Zimmet P, O'Dea K (1994b) The effect of restricting energy intake on diabetes in *Psammomys obesus*. *Int J Obesity* 18: 789-794.

Barnett M, Collier G R, Zimmet P, O'Dea K (1995) Energy intake with respect to the development of diabetes mellitus in *Psammomys obesus*. *Diabete Nutr Metab* 8: 42-47.

Bennett S A, Magnus P (1994) Trends in cardiovascular risk factors in Australia: Results from the National Heart Foundation's Risk Factor Prevalence Study, 1980-1989. *Med J Aust* 161: 519-527.

Bouchard C. The genetics of obesity.Boca Raton: CRC Press, 1994.

Ciechanover A, Schwartz A L (1994) The ubiquitin-mediated proteolytic pathway: mechanisms of recognition of the proteolytic substrate and involvement in the degradation of native cellular proteins. *FASEB J* 8: 182-191.

Collier G R, de Silva A, Sanigorski A, Walder K, Yamamoto A, Zimmet P (1997a) Development of obesity and insulin resistance in the Israeli Sand Rat (*Psammomys obesus*): Does leptin play a role. *Ann New York Acad Sci* 827: 50-63.

Collier G R, Walder K, de Silva A, Morton G, Zimmet P (1997b) Diabetes, obesity and leptin in the Israeli Sand Rat (*Psammomys obesus*). *Exp Clin Endocrinol Diabetes* 105: 36-37.

DeFronzo R A (1988) The triumvirate B-cell, muscle and liver: A collusion responsible for NIDDM. *Diabetes* 37: 667-688.

Kopelman P G, Finer N, Fox K R, Hill A, MacDonald I A (1994) ASO consensus statement on obesity. *Int J Obesity* 18: 188-191.

Leibowitz S F (1985) Brain monoamines and peptides: Role in the control of eating behaviour. *Fed Proc* 45: 1396-1403.

Liang P, Pardee A B (1992) Differential display of eukaryotic messenger RNA by means of the polymerase chain reaction. *Science* 257: 967-971.

National Health and Medical Research Council (1996) Acting on Australia's weight: A strategy for the prevention of overweight and obesity.Canberra: National Health and Medical Research Council.

Needleman and Wunsch (1970) *J. Mol. Biol.* 48: 443-453.

Risk Factor Prevalence Study Management Committee. Risk Factor Prevalence Study: Survey No. 3 1989. Canberra: National Heart Foundation of Australia and Australian Institute of Health, 1990.

Ravussin E (1995) Metabolic differences and the development of obesity. *Metabolism* 44(*Suppl* 3): 12-14.

Shafrir E, Gutman A (1993) *Psammomys obesus* of the Jerusalem colony: A model for nutritionally induced, non-insulin-dependent diabetes. *J Basic Clin Physiol Pharm* 4: 83-99.

Stellar E (1954) The physiology of motivation. *Psychol Rev* 61: 5-22.

Walder K, Dascaliuc C R, Lewandowski P A, Sanigorski A J, Zimmet P, Collier GR (1997a) The effect of dietary energy restriction on the development of obesity and non-insulin-dependent diabetes mellitus (NIDDM) in *Psammomys obesus. Obesity Res* 5: 193-200.

Walder K, Lewandowski P, Morton G, Sanigorski A, de Silva A, Zimmet P, Collier G R (1997b) Effects of leptin administration in a polygenic, hyperleptinemic animal model of obesity and NIDDM: *Psammomys obesus*. Int. J. Obesity 22: 1-7, 1998.

Waters A-M, Bennett S. Risk Factors for cardiovascular disease: A summary of Australian data.Canberra: Australian Institute of Health and Welfare, 1995.

Zhang Y, Proenca R, Maffei M, Barone M, Leopold L, Friedman J M (1994) Positional cloning of the mouse obese gene and its human homologue. *Nature* 372: 425-432.

Zimmet P Z (1992) Kelly West Lecture: 1991. Challenges in diabetes epidemiology-From West to the Rest. *Diabetes Care* 15(2): 232-247.

The invention claimed is:

1. An isolated protein which is produced in a larger amount in hypothalamus tissue of obese animals as compared to lean animals and stimulates weight gain comprising the amino acid sequence of SEQ ID NO: 14 or an amino acid sequence encoded by a nucleotide sequence that is capable of hybridizing to a nucleotide sequence encoding SEQ ID NO: 14 under high stringency conditions of at least 31% v/v to at least about 50% v/v formamide, from at least 0.01M to at least about 0.15M salt for hybridization at 42° C., and at least about 0.01M to at least about 0.15M salt for washing conditions at 42° C.

2. An isolated protein which is produced in a larger amount in hypothalamus tissue of obese animals as compared to lean animals and stimulates weight gain, said protein being encoded by the nucleotide sequence of SEQ ID NO: 13 or a nucleotide sequence that is capable of hybridizing to SEQ ID NO: 13 under high stringency conditions of at least 31% v/v to at least about 50% v/v formamide, from at least 0.01M to at least about 0.15M salt for hybridization at 42° C., and at least about 0.01M to at least about 0.15M salt for washing conditions at 42° C.

3. A composition comprising a protein according to claim 1 or 2 or an agonist or antagonist thereof together with one or more pharmaceutically acceptable carriers and/or diluents.

* * * * *

SEQUENCE LISTING

```
<160> NUMBER OF SEQ ID NOS: 22

<210> SEQ ID NO 1
<211> LENGTH: 370
<212> TYPE: DNA
<213> ORGANISM: Psammomys obesus
<220> FEATURE:
<221> NAME/KEY: CDS
<222> LOCATION: (29)..(247)

<400> SEQUENCE: 1
gttccaggag attacagctc cagccaca atg att gag gtg gtt tgc aac gac         52
                                Met Ile Glu Val Val Cys Asn Asp
                                 1               5 cgt cta gga aag aaa gtc cgc gtt aag tgc aac acc gat gac acc atc       100
Arg Leu Gly Lys Lys Val Arg Val Lys Cys Asn Thr Asp Asp Thr Ile
     10              15                  20 ggg gac ttg aag aaa ctg ata gcg gcc caa act ggc act cgt tgg aat       148
Gly Asp Leu Lys Lys Leu Ile Ala Ala Gln Thr Gly Thr Arg Trp Asn
 25                  30                  35                  40 aag atc gtt ctt aaa aag tgg tac acg att ttt aag gac cat gta tct       196
Lys Ile Val Leu Lys Lys Trp Tyr Thr Ile Phe Lys Asp His Val Ser
                 45                  50                  55 ctg gga gat tat gaa atc cac gat ggg atg aac ctg gag ctt tat tac       244
Leu Gly Asp Tyr Glu Ile His Asp Gly Met Asn Leu Glu Leu Tyr Tyr
             60                  65                  70 cag tagagggaa ttcctccacc ttgcccaacc ttgctttcct ctcccatggc              297
Gln tcatttaaca ctgttgtaga tgctcatttt taacaattca catgaataaa aactttgatg      357
ctgcaaaaaa aaa                                                         370

<210> SEQ ID NO 2
<211> LENGTH: 73
<212> TYPE: PRT
<213> ORGANISM: Psammomys obesus

<400> SEQUENCE: 2

Met Ile Glu Val Val Cys Asn Asp Arg Leu Gly Lys Lys Val Arg Val
 1               5                  10                  15

Lys Cys Asn Thr Asp Asp Thr Ile Gly Asp Leu Lys Lys Leu Ile Ala
             20                  25                  30
```

```
Ala Gln Thr Gly Thr Arg Trp Asn Lys Ile Val Leu Lys Lys Trp Tyr
            35                  40                  45

Thr Ile Phe Lys Asp His Val Ser Leu Gly Asp Tyr Glu Ile His Asp
        50                  55                  60

Gly Met Asn Leu Glu Leu Tyr Tyr Gln
 65                  70
```

```
<210> SEQ ID NO 3
<211> LENGTH: 342
<212> TYPE: DNA
<213> ORGANISM: Psammomys obesus

<400> SEQUENCE: 3
tcatgtgaat tgttaaaaat gagcatctac aacagtgtta atgagccat gggagaggaa    60 agcaaggttg ggcaaggtgg aggaattccc ctctactggt aataaagctc caggttcatc   120
ccatcgtgga tttcataatc tcccagagat acatggtcct taaaaatcgt gtaccacttt   180
ttaagaacga tcttattcca acgagtgcca gtttgggccg ctatcagttt cttcaagtcc   240
ccgatggtgt catcggtgtt gcacttaacg cggactttct ttcctagacg gtcgttgcaa   300
accacctcaa tcattgtggc tggagctgta atctcctgga ac                     342

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagctttttt tttttg                                                   16

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagcttcggg taa                                                      13

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtccgcgtt aagtgcaaca                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```
ctccaggttc atcccatcgt 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctacagct tcaccaccac 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcttgctgat ccacatctgc 20

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggtaataaa gctccaggtt catcccatcg 30

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caaactggca ctcgttggaa 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttgggcaag gtggaggaa 19

<210> SEQ ID NO 13
<211> LENGTH: 102
<212> TYPE: DNA
<213> ORGANISM: Homo sapiens
<220> FEATURE:
<221> NAME/KEY: CDS
<222> LOCATION: (1)..(99)
<220> FEATURE:
<221> NAME/KEY: modified_base
<222> LOCATION: (44)

<223> OTHER INFORMATION: a, c, g, or t

<400> SEQUENCE: 13

```
atg atc gag gtt gtt tgc aac gac cgt ctg ggg aaa aag gtc cnc gtt      48
Met Ile Glu Val Val Cys Asn Asp Arg Leu Gly Lys Lys Val Xaa Val
 1               5                  10                  15 aaa tgc aac acg gat gat acc atc ggg gac ctt aag aag ctg att gca      96
Lys Cys Asn Thr Asp Asp Thr Ile Gly Asp Leu Lys Lys Leu Ile Ala
            20                  25                  30 gcc taa                                                             102
Ala
```

<210> SEQ ID NO 14
<211> LENGTH: 33
<212> TYPE: PRT
<213> ORGANISM: Homo sapiens
<220> FEATURE:
<221> NAME/KEY: MOD_RES
<222> LOCATION: (15)
<223> OTHER INFORMATION: Leu, Pro, His, or Arg

<400> SEQUENCE: 14

```
Met Ile Glu Val Val Cys Asn Asp Arg Leu Gly Lys Lys Val Xaa Val
 1               5                  10                  15

Lys Cys Asn Thr Asp Asp Thr Ile Gly Asp Leu Lys Lys Leu Ile Ala
            20                  25                  30

Ala
```

<210> SEQ ID NO 15
<211> LENGTH: 73
<212> TYPE: PRT
<213> ORGANISM: Homo sapiens

<400> SEQUENCE: 15

```
Met Ile Glu Val Val Cys Asn Asp Arg Leu Gly Lys Lys Val Arg Val
 1               5                  10                  15

Lys Cys Asn Thr Asp Asp Thr Ile Gly Asp Leu Lys Lys Leu Ile Ala
            20                  25                  30

Ala Gln Thr Gly Thr Arg Trp Asn Lys Ile Val Leu Lys Lys Trp Tyr
            35                  40                  45

Thr Ile Phe Lys Asp His Val Ser Leu Gly Asp Tyr Glu Ile His Asp
        50                  55                  60

Gly Met Asn Leu Glu Leu Tyr Tyr Gln
 65                  70
```

<210> SEQ ID NO 16
<211> LENGTH: 73
<212> TYPE: PRT
<213> ORGANISM: Mus musculus

<400> SEQUENCE: 16

```
Met Ile Glu Val Val Cys Asn Asp Arg Leu Gly Lys Lys Val Arg Val
 1               5                  10                  15

Lys Cys Asn Thr Asp Asp Thr Ile Gly Asp Leu Lys Lys Leu Ile Ala
            20                  25                  30

Ala Gln Thr Gly Thr Arg Trp Asn Lys Ile Val Leu Lys Lys Trp Tyr
            35                  40                  45

Thr Ile Phe Lys Asp His Val Ser Leu Gly Asp Tyr Glu Ile His Asp
        50                  55                  60

Gly Met Asn Leu Glu Leu Tyr Tyr Gln
```

```
                                     65                  70

<210> SEQ ID NO 17
<211> LENGTH: 73
<212> TYPE: PRT
<213> ORGANISM: Caenorhabditis elegans

<400> SEQUENCE: 17

Met Ile Glu Ile Thr Val Asn Asp Arg Leu Gly Lys Lys Val Arg Ile
  1               5                  10                  15

Lys Cys Asn Pro Ser Asp Thr Ile Gly Asp Leu Lys Lys Leu Ile Ala
                 20                  25                  30

Ala Gln Thr Gly Thr Arg Trp Glu Lys Ile Val Leu Lys Lys Trp Tyr
             35                  40                  45

Thr Ile Tyr Lys Asp His Ile Thr Leu Met Asp Tyr Glu Ile His Glu
         50                  55                  60

Gly Phe Asn Phe Glu Leu Tyr Tyr Gln
 65                  70

<210> SEQ ID NO 18
<211> LENGTH: 66
<212> TYPE: PRT
<213> ORGANISM: Fasciola hepatica

<400> SEQUENCE: 18

Asp Arg Leu Gly Lys Lys Val Arg Val Lys Cys Asn Pro Thr Asp Lys
  1               5                  10                  15

Val Gly Asp Leu Lys Lys Leu Ile Ala Ala Gln Thr Gly Thr Ala Pro
                 20                  25                  30

Glu Arg Ile Val Leu Lys Lys Trp Tyr Thr Ile Tyr Lys Asp His Val
             35                  40                  45

Thr Leu Arg Asp Tyr Glu Ile Asn Asp Gly Met Asn Leu Glu Leu Tyr
         50                  55                  60

Tyr Gln
 65

<210> SEQ ID NO 19
<211> LENGTH: 73
<212> TYPE: PRT
<213> ORGANISM: Oryza sativa

<400> SEQUENCE: 19

Met Ile Glu Val Val Cys Asn Asp Arg Leu Gly Lys Lys Val Arg Val
  1               5                  10                  15

Lys Cys Asn Thr Asp Asp Thr Ile Gly Asp Leu Lys Lys Leu Ile Ala
                 20                  25                  30

Ala Gln Thr Gly Thr Arg Trp Asn Lys Ile Val Leu Lys Lys Trp Tyr
             35                  40                  45

Thr Ile Tyr Lys Asp His Ile Thr Leu Ala Asp Tyr Glu Ile His Asp
         50                  55                  60

Gly Met Gly Leu Glu Leu Tyr Tyr Asn
 65                  70

<210> SEQ ID NO 20
<211> LENGTH: 73
<212> TYPE: PRT
<213> ORGANISM: Saccharomyces cerevisiae

<400> SEQUENCE: 20
```

```
Met Ile Glu Val Val Cys Asn Asp Arg Leu Gly Lys Lys Val Arg Val
 1               5                  10                  15

Lys Cys Asn Thr Asp Asp Thr Ile Gly Asp Leu Lys Lys Leu Ile Ala
                20                  25                  30

Ala Gln Thr Gly Thr Arg Trp Asn Lys Ile Val Leu Lys Lys Trp Tyr
            35                  40                  45

Thr Ile Leu Lys Asp His Ile Cys Leu Glu Asp Tyr Glu Val His Asp
        50                  55                  60

Gln Thr Asn Leu Glu Leu Tyr Tyr Leu
 65                  70

<210> SEQ ID NO 21
<211> LENGTH: 76
<212> TYPE: PRT
<213> ORGANISM: Homo sapiens

<400> SEQUENCE: 21

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
 65                  70                  75

<210> SEQ ID NO 22
<211> LENGTH: 60
<212> TYPE: PRT
<213> ORGANISM: Arabidopsis thaliana

<400> SEQUENCE: 22

Gly Lys Thr Ile Ile Leu Glu Val Glu Ser Ser Asp Thr Ile Ala Asn
 1               5                  10                  15

Val Lys Glu Lys Ile Gln Val Lys Glu Gly Ile Lys Pro Asp Gln Gln
                20                  25                  30

Met Leu Ile Phe Phe Gly Gln Gln Leu Glu Asp Gly Val Thr Leu Gly
            35                  40                  45

Asp Tyr Asp Ile His Lys Lys Ser Thr Leu Tyr Leu
        50                  55                  60
```